(12) United States Patent
Sondermann et al.

(10) Patent No.: US 12,048,728 B2
(45) Date of Patent: *Jul. 30, 2024

(54) HIGHLY CONCENTRATED FORMULATIONS OF SOLUBLE Fc RECEPTORS

(71) Applicant: SUPPREMOL GMBH, Martinsried (DE)

(72) Inventors: Peter Sondermann, Stockdorf (DE); Thomas Pohl, Neuried (DE)

( * ) Notice: Subject to any disclaimer, the term of this patent is extended or adjusted under 35 U.S.C. 154(b) by 72 days.

This patent is subject to a terminal disclaimer.

(21) Appl. No.: 17/583,503

(22) Filed: Jan. 25, 2022

(65) Prior Publication Data

US 2022/0296668 A1  Sep. 22, 2022

Related U.S. Application Data

(63) Continuation of application No. 16/240,504, filed on Jan. 4, 2019, now Pat. No. 11,266,708, which is a continuation of application No. 14/787,097, filed as application No. PCT/EP2014/001029 on Apr. 16, 2014, now Pat. No. 10,226,504.

(30) Foreign Application Priority Data

Apr. 26, 2013 (EP) ..................... 13002211

(51) Int. Cl.
| | |
|---|---|
| *A61K 38/00* | (2006.01) |
| *A61K 9/00* | (2006.01) |
| *A61K 9/19* | (2006.01) |
| *A61K 38/17* | (2006.01) |
| *A61K 47/02* | (2006.01) |
| *A61K 47/12* | (2006.01) |
| *A61K 47/18* | (2017.01) |
| *A61K 47/26* | (2006.01) |
| *A61P 37/00* | (2006.01) |

(52) U.S. Cl.
CPC ............ *A61K 38/00* (2013.01); *A61K 9/0019* (2013.01); *A61K 9/19* (2013.01); *A61K 38/1774* (2013.01); *A61K 47/02* (2013.01); *A61K 47/12* (2013.01); *A61K 47/183* (2013.01); *A61K 47/26* (2013.01); *A61P 37/00* (2018.01)

(58) Field of Classification Search
None
See application file for complete search history.

*Primary Examiner* — Marianne P Allen

(57) ABSTRACT

The present invention relates to novel formulations of soluble Fc receptors and especially to formulations containing high concentrations of soluble FcγRIIB receptor. The invention further relates to the use of such formulations as pharmaceutical compounds for the treatment of autoimmune diseases, infections and other conditions where the immune system is involved.

8 Claims, 16 Drawing Sheets

Specification includes a Sequence Listing.

*60 mg/mL instead of 80 mg/mL in case of 40% Sucrose

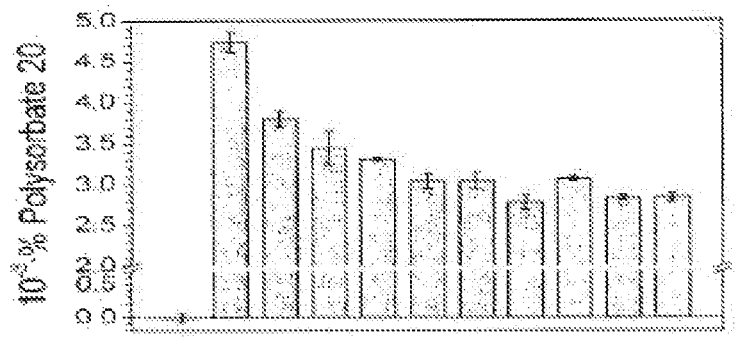
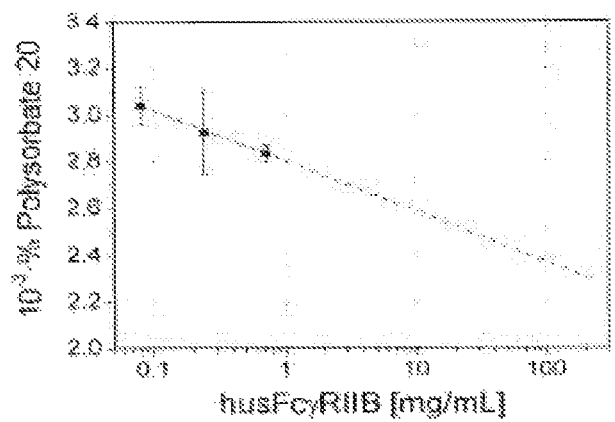
Figure 8A
Figure 8B

Figure 11

Table 2

| husFc γRIIB [mg/mL] | pH | Sugar [%] | NaCl [mM] | Osmolality [mOsm/kg] | 0 d | 1 d | 8 d | 14 d | 29 d | Sum |
|---|---|---|---|---|---|---|---|---|---|---|
| 70 | 5.5 | 0 | 10 | 24 | 0 | 0 | 0 | 0 | 0 | 0 |
| 70 | 6.0 | 0 | 10 | 24 | 1 | 3 | 4 | 4 | 4 | 16 |
| 70 | 6.5 | 0 | 10 | 24 | 2 | 5 | 5 | 5 | 5 | 22 |
| 70 | 7.0 | 0 | 10 | 24 | 1 | 5 | 5 | 5 | 5 | 21 |
| 70 | 7.5 | 0 | 10 | 24 | 0 | 0 | 5 | 5 | 5 | 15 |
| 70 | 5.5 | 3 | 10 | 137 | 0 | 0 | 0 | 0 | 0 | 0 |
| 70 | 6.0 | 3 | 10 | 137 | 0 | 0 | 2 | 3 | 3 | 8 |
| 70 | 6.5 | 3 | 10 | 137 | 0 | 5 | 5 | 5 | 5 | 20 |
| 70 | 7.0 | 3 | 10 | 137 | 0 | 0 | 0 | 0 | 5 | 5 |
| 70 | 7.5 | 3 | 10 | 137 | 0 | 0 | 5 | 5 | 5 | 15 |
| 70 | 5.5 | 0 | 50 | 104 | 0 | 0 | 0 | 0 | 0 | 0 |
| 70 | 6.0 | 0 | 50 | 104 | 0 | 2 | 3 | 3 | 3 | 11 |
| 70 | 6.5 | 0 | 50 | 104 | 0 | 0 | 0 | 0 | 5 | 5 |
| 70 | 7.0 | 0 | 50 | 104 | 0 | 0 | 0 | 0 | 1 | 1 |
| 70 | 7.5 | 0 | 50 | 104 | 0 | 0 | 4 | 4 | 4 | 12 |
| 70 | 5.5 | 3 | 50 | 217 | 0 | 0 | 0 | 0 | 0 | 0 |
| 70 | 6.0 | 3 | 50 | 217 | 0 | 0 | 0 | 0 | 2 | 2 |
| 70 | 6.5 | 3 | 50 | 217 | 0 | 0 | 0 | 0 | 5 | 5 |
| 70 | 7.0 | 3 | 50 | 217 | 0 | 0 | 0 | 0 | 0 | 0 |
| 70 | 7.5 | 3 | 50 | 217 | 0 | 0 | 1 | 3 | 5 | 9 |
| 70 | 5.5 | 0 | 225 | 454 | 0 | 0 | 0 | 0 | 1 | 1 |
| 70 | 6.0 | 0 | 225 | 454 | 0 | 0 | 0 | 0 | 0 | 0 |
| 70 | 6.5 | 0 | 225 | 454 | 0 | 0 | 0 | 0 | 0 | 0 |
| 70 | 7.0 | 0 | 225 | 454 | 0 | 0 | 0 | 0 | 0 | 0 |
| 70 | 7.5 | 0 | 225 | 454 | 0 | 0 | 0 | 0 | 0 | 0 |
| 70 | 5.5 | 3 | 225 | 567 | 0 | 0 | 0 | 0 | 0 | 0 |
| 70 | 6.0 | 3 | 225 | 567 | 0 | 0 | 0 | 0 | 0 | 0 |
| 70 | 6.5 | 3 | 225 | 567 | 0 | 0 | 0 | 0 | 0 | 0 |
| 70 | 7.0 | 3 | 225 | 567 | 0 | 0 | 0 | 0 | 0 | 0 |
| 70 | 7.5 | 3 | 225 | 567 | 0 | 0 | 0 | 0 | 0 | 0 |

Figure 12

Table 3

| husFcγRIIB [mg/mL] | pH | Sugar [%] | NaCl [mM] | Osmolality [mOsm/kg] | 0 d | 1 d | 8 d | 14 d | 28 d | Sum |
|---|---|---|---|---|---|---|---|---|---|---|
| 100 | 5.5 | 0 | 10 | 25 | 0 | 0 | 0 | 0 | 0 | 0 |
| 100 | 6.0 | 0 | 10 | 25 | 5 | 5 | 5 | 5 | 5 | 25 |
| 100 | 6.5 | 0 | 10 | 25 | 0 | 5 | 5 | 5 | 5 | 20 |
| 100 | 7.0 | 0 | 10 | 25 | 0 | 1 | 4 | 4 | 5 | 14 |
| 100 | 7.5 | 0 | 10 | 25 | 0 | 0 | 0 | 0 | 0 | 0 |
| 100 | 5.5 | 3 | 10 | 138 | 0 | 0 | 0 | 0 | 0 | 0 |
| 100 | 6.0 | 3 | 10 | 138 | 1 | 4 | 4 | 4 | 4 | 17 |
| 100 | 6.5 | 3 | 10 | 138 | 0 | 5 | 5 | 5 | 5 | 20 |
| 100 | 7.0 | 3 | 10 | 138 | 3 | 5 | 5 | 5 | 5 | 23 |
| 100 | 7.5 | 3 | 10 | 138 | 2 | 2 | 2 | 2 | 4 | 12 |
| 100 | 5.5 | 0 | 50 | 105 | 0 | 0 | 0 | 0 | 1 | 1 |
| 100 | 6.0 | 0 | 50 | 105 | 0 | 3 | 3 | 4 | 4 | 14 |
| 100 | 6.5 | 0 | 50 | 105 | 5 | 5 | 5 | 5 | 5 | 25 |
| 100 | 7.0 | 0 | 50 | 105 | 4 | 5 | 5 | 5 | 5 | 24 |
| 100 | 7.5 | 0 | 50 | 105 | 2 | 3 | 1 | 0 | 1 | 7 |
| 100 | 5.5 | 3 | 50 | 218 | 0 | 0 | 0 | 0 | 0 | 0 |
| 100 | 6.0 | 3 | 50 | 218 | 1 | 4 | 4 | 4 | 4 | 17 |
| 100 | 6.5 | 3 | 50 | 218 | 4 | 5 | 5 | 5 | 5 | 24 |
| 100 | 7.0 | 3 | 50 | 218 | 0 | 0 | 0 | 0 | 4 | 4 |
| 100 | 7.5 | 3 | 50 | 218 | 0 | 0 | 0 | 0 | 1 | 1 |
| 100 | 5.5 | 0 | 225 | 455 | 0 | 0 | 0 | 0 | 0 | 0 |
| 100 | 6.0 | 0 | 225 | 455 | 0 | 0 | 0 | 0 | 0 | 0 |
| 100 | 6.5 | 0 | 225 | 455 | 0 | 0 | 0 | 0 | 1 | 1 |
| 100 | 7.0 | 0 | 225 | 455 | 0 | 0 | 0 | 0 | 0 | 0 |
| 100 | 7.5 | 0 | 225 | 455 | 0 | 0 | 0 | 0 | 0 | 0 |
| 100 | 5.5 | 3 | 225 | 568 | 0 | 0 | 0 | 0 | 0 | 0 |
| 100 | 6.0 | 3 | 225 | 568 | 0 | 0 | 0 | 0 | 0 | 0 |
| 100 | 6.5 | 3 | 225 | 568 | 2 | 2 | 3 | 3 | 3 | 13 |
| 100 | 7.0 | 3 | 225 | 568 | 0 | 0 | 0 | 0 | 0 | 0 |
| 100 | 7.5 | 3 | 225 | 568 | 0 | 0 | 0 | 0 | 0 | 0 |

Figure 13

Table 4

| husFc γRIIB [mg/mL] | pH | Sugar [%] | NaCl [mM] | Osmolality [mOsm/kg] | 0 d | 7 d | 14 d | 28 d | Sum |
|---|---|---|---|---|---|---|---|---|---|
| 120 | 5.5 | 6 | 50 | 332 | 0 | 0 | 0 | 0 | 0 |
| 120 | 6.0 | 6 | 50 | 332 | 0 | 0 | 0 | 3 | 3 |
| 120 | 6.5 | 6 | 50 | 332 | 0 | 0 | 0 | 4 | 4 |
| 120 | 7.0 | 6 | 50 | 332 | 0 | 0 | 0 | 0 | 0 |
| 120 | 7.5 | 6 | 50 | 332 | 0 | 0 | 1 | 1 | 2 |
| 120 | 5.5 | 4.5 | 75 | 326 | 0 | 1 | 1 | 2 | 4 |
| 120 | 6.0 | 4.5 | 75 | 326 | 0 | 0 | 1 | 1 | 2 |
| 120 | 6.5 | 4.5 | 75 | 326 | 0 | 0 | 4 | 4 | 8 |
| 120 | 7.0 | 4.5 | 75 | 326 | 0 | 0 | 0 | 0 | 0 |
| 120 | 7.5 | 4.5 | 75 | 326 | 0 | 2 | 3 | 3 | 8 |
| 120 | 5.5 | 3 | 100 | 319 | 2 | 2 | 3 | 3 | 10 |
| 120 | 6.0 | 3 | 100 | 319 | 0 | 0 | 2 | 3 | 5 |
| 120 | 6.5 | 3 | 100 | 319 | 0 | 0 | 0 | 0 | 0 |
| 120 | 7.0 | 3 | 100 | 319 | 0 | 0 | 0 | 0 | 0 |
| 120 | 7.5 | 3 | 100 | 319 | 0 | 0 | 0 | 0 | 0 |
| 120 | 5.5 | 1.5 | 125 | 313 | 0 | 5 | 5 | 5 | 15 |
| 120 | 6.0 | 1.5 | 125 | 313 | 0 | 0 | 1 | 2 | 3 |
| 120 | 6.5 | 1.5 | 125 | 313 | 0 | 0 | 0 | 0 | 0 |
| 120 | 7.0 | 1.5 | 125 | 313 | 0 | 0 | 0 | 0 | 0 |
| 120 | 7.5 | 1.5 | 125 | 313 | 0 | 0 | 0 | 0 | 0 |
| 150 | 5.5 | 6 | 50 | 334 | 2 | 2 | 2 | 2 | 8 |
| 150 | 6.0 | 6 | 50 | 334 | 0 | 2 | 3 | 3 | 8 |
| 150 | 6.5 | 6 | 50 | 334 | 0 | 5 | 5 | 5 | 15 |
| 150 | 7.0 | 6 | 50 | 334 | 0 | 0 | 0 | 5 | 5 |
| 150 | 7.5 | 6 | 50 | 334 | 0 | 0 | 0 | 5 | 5 |
| 150 | 5.5 | 4.5 | 75 | 327 | 0 | 1 | 3 | 5 | 9 |
| 150 | 6.0 | 4.5 | 75 | 327 | 1 | 3 | 4 | 4 | 12 |
| 150 | 6.5 | 4.5 | 75 | 327 | 5 | 5 | 5 | 5 | 20 |
| 150 | 7.0 | 4.5 | 75 | 327 | 5 | 5 | 5 | 5 | 20 |
| 150 | 7.5 | 4.5 | 75 | 327 | 4 | 5 | 5 | 5 | 19 |
| 150 | 5.5 | 3 | 100 | 321 | 0 | 5 | 5 | 5 | 15 |
| 150 | 6.0 | 3 | 100 | 321 | 5 | 5 | 5 | 5 | 20 |
| 150 | 6.5 | 3 | 100 | 321 | 4 | 5 | 5 | 5 | 19 |
| 150 | 7.0 | 3 | 100 | 321 | 3 | 5 | 5 | 5 | 18 |
| 150 | 7.5 | 3 | 100 | 321 | 0 | 0 | 0 | 0 | 0 |
| 150 | 5.5 | 1.5 | 125 | 314 | 2 | 5 | 5 | 5 | 17 |
| 150 | 6.0 | 1.5 | 125 | 314 | 3 | 5 | 5 | 5 | 18 |
| 150 | 6.5 | 1.5 | 125 | 314 | 3 | 5 | 5 | 5 | 18 |
| 150 | 7.0 | 1.5 | 125 | 314 | 3 | 5 | 5 | 5 | 18 |
| 150 | 7.5 | 1.5 | 125 | 314 | 3 | 5 | 5 | 5 | 18 |

Figure 14

Table 5

| husFcγRIIB [mg/mL] | pH | Sugar [%] | NaCl [mM] | Osmolality [mOsm/kg] | 0 d | 1 d | 8 d | 17 d | 30 d | Sum |
|---|---|---|---|---|---|---|---|---|---|---|
| 70 | 5.5 | 0 | 10 | 24 | 0 | 3 | 5 | 5 | 5 | 18 |
| 70 | 6.0 | 0 | 10 | 24 | 0 | 1 | 2 | 3 | 3 | 9 |
| 70 | 6.5 | 0 | 10 | 24 | 0 | 0 | 0 | 0 | 0 | 0 |
| 70 | 7.0 | 0 | 10 | 24 | 0 | 0 | 0 | 0 | 0 | 0 |
| 70 | 7.5 | 0 | 10 | 24 | 0 | 0 | 0 | 0 | 0 | 0 |
| 70 | 5.5 | 3 | 10 | 137 | 0 | 0 | 3 | 4 | 5 | 12 |
| 70 | 6.0 | 3 | 10 | 137 | 0 | 0 | 0 | 1 | 1 | 2 |
| 70 | 6.5 | 3 | 10 | 137 | 0 | 0 | 0 | 0 | 0 | 0 |
| 70 | 7.0 | 3 | 10 | 137 | 0 | 0 | 0 | 0 | 0 | 0 |
| 70 | 7.5 | 3 | 10 | 137 | 0 | 0 | 0 | 0 | 0 | 0 |
| 70 | 5.5 | 0 | 50 | 104 | 0 | 2 | 4 | 5 | 5 | 16 |
| 70 | 6.0 | 0 | 50 | 104 | 0 | 1 | 1 | 1 | 2 | 5 |
| 70 | 6.5 | 0 | 50 | 104 | 0 | 0 | 0 | 0 | 0 | 0 |
| 70 | 7.0 | 0 | 50 | 104 | 0 | 0 | 0 | 0 | 0 | 0 |
| 70 | 7.5 | 0 | 50 | 104 | 0 | 0 | 0 | 0 | 0 | 0 |
| 70 | 5.5 | 3 | 50 | 217 | 0 | 1 | 2 | 3 | 4 | 10 |
| 70 | 6.0 | 3 | 50 | 217 | 0 | 0 | 0 | 0 | 0 | 0 |
| 70 | 6.5 | 3 | 50 | 217 | 0 | 0 | 0 | 0 | 0 | 0 |
| 70 | 7.0 | 3 | 50 | 217 | 0 | 0 | 0 | 0 | 0 | 0 |
| 70 | 7.5 | 3 | 50 | 217 | 0 | 0 | 0 | 0 | 0 | 0 |
| 70 | 5.5 | 0 | 225 | 454 | 0 | 2 | 3 | 4 | 4 | 13 |
| 70 | 6.0 | 0 | 225 | 454 | 0 | 0 | 0 | 0 | 0 | 0 |
| 70 | 6.5 | 0 | 225 | 454 | 0 | 0 | 0 | 0 | 0 | 0 |
| 70 | 7.0 | 0 | 225 | 454 | 0 | 0 | 0 | 0 | 0 | 0 |
| 70 | 7.5 | 0 | 225 | 454 | 0 | 0 | 0 | 0 | 0 | 0 |
| 70 | 5.5 | 3 | 225 | 567 | 0 | 0 | 0 | 1 | 1 | 2 |
| 70 | 6.0 | 3 | 225 | 567 | 0 | 0 | 0 | 0 | 0 | 0 |
| 70 | 6.5 | 3 | 225 | 567 | 0 | 0 | 0 | 0 | 0 | 0 |
| 70 | 7.0 | 3 | 225 | 567 | 0 | 0 | 0 | 0 | 0 | 0 |
| 70 | 7.5 | 3 | 225 | 567 | 0 | 0 | 0 | 0 | 0 | 0 |

Figure 15

Table 6

| husFcγRIIB [mg/mL] | pH | Sugar [%] | NaCl [mM] | Osmolality [mOsm/kg] | 0 d | 4 d | 7 d | 15 d | 28 d | Sum |
|---|---|---|---|---|---|---|---|---|---|---|
| 100 | 5.5 | 0 | 10 | 25 | 1 | 5 | 5 | 5 | 5 | 21 |
| 100 | 6.0 | 0 | 10 | 25 | 1 | 4 | 5 | 5 | 5 | 20 |
| 100 | 6.5 | 0 | 10 | 25 | 0 | 1 | 1 | 1 | 2 | 5 |
| 100 | 7.0 | 0 | 10 | 25 | 0 | 0 | 0 | 0 | 0 | 0 |
| 100 | 7.5 | 0 | 10 | 25 | 0 | 0 | 0 | 0 | 0 | 0 |
| 100 | 5.5 | 3 | 10 | 138 | 0 | 3 | 4 | 4 | 5 | 16 |
| 100 | 6.0 | 3 | 10 | 138 | 0 | 1 | 3 | 4 | 5 | 13 |
| 100 | 6.5 | 3 | 10 | 138 | 0 | 0 | 0 | 0 | 0 | 0 |
| 100 | 7.0 | 3 | 10 | 138 | 0 | 0 | 0 | 0 | 0 | 0 |
| 100 | 7.5 | 3 | 10 | 138 | 0 | 0 | 0 | 0 | 0 | 0 |
| 100 | 5.5 | 0 | 50 | 105 | 0 | 5 | 5 | 5 | 5 | 20 |
| 100 | 6.0 | 0 | 50 | 105 | 0 | 3 | 4 | 5 | 5 | 17 |
| 100 | 6.5 | 0 | 50 | 105 | 0 | 0 | 1 | 1 | 1 | 3 |
| 100 | 7.0 | 0 | 50 | 105 | 0 | 0 | 0 | 0 | 0 | 0 |
| 100 | 7.5 | 0 | 50 | 105 | 0 | 0 | 0 | 0 | 0 | 0 |
| 100 | 5.5 | 3 | 50 | 218 | 0 | 0 | 3 | 4 | 5 | 12 |
| 100 | 6.0 | 3 | 50 | 218 | 0 | 0 | 0 | 0 | 3 | 3 |
| 100 | 6.5 | 3 | 50 | 218 | 0 | 0 | 0 | 0 | 0 | 0 |
| 100 | 7.0 | 3 | 50 | 218 | 0 | 0 | 0 | 0 | 0 | 0 |
| 100 | 7.5 | 3 | 50 | 218 | 0 | 0 | 0 | 0 | 0 | 0 |
| 100 | 5.5 | 0 | 225 | 455 | 0 | 3 | 4 | 4 | 4 | 15 |
| 100 | 6.0 | 0 | 225 | 455 | 0 | 1 | 1 | 2 | 3 | 7 |
| 100 | 6.5 | 0 | 225 | 455 | 0 | 0 | 0 | 0 | 0 | 0 |
| 100 | 7.0 | 0 | 225 | 455 | 0 | 0 | 0 | 0 | 0 | 0 |
| 100 | 7.5 | 0 | 225 | 455 | 0 | 0 | 0 | 0 | 0 | 0 |
| 100 | 5.5 | 3 | 225 | 568 | 0 | 0 | 1 | 3 | 4 | 8 |
| 100 | 6.0 | 3 | 225 | 568 | 0 | 0 | 0 | 0 | 0 | 0 |
| 100 | 6.5 | 3 | 225 | 568 | 0 | 0 | 0 | 0 | 0 | 0 |
| 100 | 7.0 | 3 | 225 | 568 | 0 | 0 | 0 | 0 | 0 | 0 |
| 100 | 7.5 | 3 | 225 | 568 | 0 | 0 | 0 | 0 | 0 | 0 |

Figure 16

Table 7

| husFcγRIIB [mg/mL] | pH | Sugar [%] | NaCl [mM] | Osmolality [mOsm/kg] | 0 d | 7 d | 14 d | 28 d | Sum |
|---|---|---|---|---|---|---|---|---|---|
| 120 | 6.0 | 7.5 | 25 | 339 | 0 | 1 | 2 | 3 | 6 |
| 120 | 6.5 | 7.5 | 25 | 339 | 0 | 0 | 0 | 0 | 0 |
| 120 | 7.0 | 7.5 | 25 | 339 | 0 | 0 | 0 | 0 | 0 |
| 120 | 7.5 | 7.5 | 25 | 339 | 0 | 0 | 0 | 0 | 0 |
| 120 | 6.0 | 6 | 50 | 332 | 0 | 2 | 3 | 4 | 9 |
| 120 | 6.5 | 6 | 50 | 332 | 0 | 0 | 0 | 0 | 0 |
| 120 | 7.0 | 6 | 50 | 332 | 0 | 0 | 0 | 0 | 0 |
| 120 | 7.5 | 6 | 50 | 332 | 0 | 0 | 0 | 0 | 0 |
| 120 | 6.0 | 4.5 | 75 | 326 | 0 | 0 | 0 | 0 | 0 |
| 120 | 6.5 | 4.5 | 75 | 326 | 0 | 0 | 0 | 0 | 0 |
| 120 | 7.0 | 4.5 | 75 | 326 | 0 | 0 | 0 | 0 | 0 |
| 120 | 7.5 | 4.5 | 75 | 326 | 0 | 0 | 0 | 0 | 0 |
| 120 | 6.0 | 3 | 100 | 319 | 0 | 2 | 3 | 3 | 8 |
| 120 | 6.5 | 3 | 100 | 319 | 0 | 0 | 0 | 0 | 0 |
| 120 | 7.0 | 3 | 100 | 319 | 0 | 0 | 0 | 0 | 0 |
| 120 | 7.5 | 3 | 100 | 319 | 0 | 0 | 0 | 0 | 0 |
| 120 | 6.0 | 1.5 | 125 | 313 | 0 | 1 | 2 | 2 | 5 |
| 120 | 6.5 | 1.5 | 125 | 313 | 0 | 0 | 0 | 0 | 0 |
| 120 | 7.0 | 1.5 | 125 | 313 | 0 | 0 | 0 | 0 | 0 |
| 120 | 7.5 | 1.5 | 125 | 313 | 0 | 0 | 0 | 0 | 0 |
| 150 | 6.0 | 7.5 | 25 | 340 | 0 | 2 | 3 | 4 | 9 |
| 150 | 6.5 | 7.5 | 25 | 340 | 0 | 0 | 0 | 0 | 0 |
| 150 | 7.0 | 7.5 | 25 | 340 | 0 | 0 | 0 | 0 | 0 |
| 150 | 7.5 | 7.5 | 25 | 340 | 0 | 0 | 0 | 0 | 0 |
| 150 | 6.0 | 6 | 50 | 334 | 0 | 1 | 2 | 4 | 7 |
| 150 | 6.5 | 6 | 50 | 334 | 0 | 0 | 0 | 0 | 0 |
| 150 | 7.0 | 6 | 50 | 334 | 0 | 0 | 0 | 0 | 0 |
| 150 | 7.5 | 6 | 50 | 334 | 0 | 0 | 0 | 0 | 0 |
| 150 | 6.0 | 4.5 | 75 | 327 | 0 | 0 | 2 | 3 | 5 |
| 150 | 6.5 | 4.5 | 75 | 327 | 0 | 0 | 0 | 0 | 0 |
| 150 | 7.0 | 4.5 | 75 | 327 | 0 | 0 | 0 | 0 | 0 |
| 150 | 7.5 | 4.5 | 75 | 327 | 0 | 0 | 0 | 0 | 0 |
| 150 | 6.0 | 3 | 100 | 321 | 0 | 0 | 0 | 0 | 0 |
| 150 | 6.5 | 3 | 100 | 321 | 0 | 0 | 0 | 1 | 1 |
| 150 | 7.0 | 3 | 100 | 321 | 0 | 0 | 0 | 0 | 0 |
| 150 | 7.5 | 3 | 100 | 321 | 0 | 0 | 0 | 0 | 0 |
| 150 | 6.0 | 1.5 | 125 | 314 | 0 | 1 | 2 | 2 | 5 |
| 150 | 6.5 | 1.5 | 125 | 314 | 0 | 0 | 0 | 0 | 0 |
| 150 | 7.0 | 1.5 | 125 | 314 | 0 | 0 | 0 | 0 | 0 |
| 150 | 7.5 | 1.5 | 125 | 314 | 0 | 0 | 0 | 0 | 0 |

HIGHLY CONCENTRATED FORMULATIONS OF SOLUBLE Fc RECEPTORS

CROSS-REFERENCE TO RELATED APPLICATIONS

This application is a continuation of U.S. patent application Ser. No. 16/240,504, filed Jan. 4, 2019, which is a continuation of U.S. patent application Ser. No. 14/787,097, filed Jan. 8, 2016, which is a 371 of PCT/EP2014/001029, filed Apr. 16, 2014, which claims the benefit of EP Patent Application No. 13002211.4, filed Apr. 26, 2013. The entire contents of each of these applications are incorporated by reference herein.

SEQUENCE LISTING

This application contains a sequence listing having the filename 29200_17583503_1-25-2022_SEQ.txt, which is an 21,401.6 byte ASCII text file that was created on Jan. 25, 2022. The entire content of this sequence listing is incorporated herein by reference

BRIEF DESCRIPTION OF THE DRAWINGS

FIGS. 8A and 8B depicts determination of free polysorbate 20 in the presence of husFcγRIIB. husFcγRIIB in 10 mM citrate, 25 mM NaCl, 3% sucrose, 1.5% mannitol, 0.005% polysorbate 20, pH 6.7 was incubated for 1 h at 25° C. (native husFcγRIIB) and 60° C. (denatured husFcγRIIB). After husFcγRIIB was removed by cation exchange chromatography (CEX), the amount of polysorbate 20 was measured (FIG. 8A). The blank represents buffer without added husFcγRIIB or detergent. The system suitability tests (SST) represent buffer with 0.005% polysorbate 20, SST2 was CEX treated and SST1 not. The measured polysorbate content at 0.08-0.72 mg/mL husFcγRIIB was extrapolated to husFcγRIIB concentrations above 10 mg/mL by linear regression ($R^2>0.998$) of the polysorbate concentration versus the logarithmic husFcγRIIB concentration (FIG. 8B).

FIG. 11 shows Table 2; Histidine based solubility screen at 70 mg/mL husFcγRIIB and 2-8° C. The visual appearance of each formulation was assessed by light microscopy and ranked according to an arbitrary scale (0=no crystals; 1=some crystals, hardly visible; 2=some crystals clearly visible; 3=more than 30 crystals per well clearly visible; 4=layer of many crystals (well not fully covered); 5=layer of many crystals (well completely covered).

FIG. 12 shows Table 3: Histidine based solubility screen at 100 mg/mL husFcγRIIB and 2-8° C. The visual appearance of each formulation was assessed by light microscopy and ranked according to an arbitrary scale (0=no crystals; 1=some crystals, hardly visible; 2=some crystals clearly visible; 3=more than 30 crystals per well clearly visible; 4=layer of many crystals (well not fully covered); 5=layer of many crystals (well completely covered).

FIG. 13 shows Table 4: Histidine based solubility screen at 120 mg/mL/150 mg/mL husFcγRIIB and 2-8° C. The visual appearance of each formulation was assessed by light microscopy and ranked according to an arbitrary scale (0=no crystals; 1=some crystals, hardly visible; 2=some crystals clearly visible; 3=more than 30 crystals per well clearly FIG. 14 shows Table 5: Citrate based solubility screen at 70 mg/mL husFcγRIIB and 2-8° C. The visual appearance of each formulation was assessed by light microscopy and ranked according to an arbitrary scale (0=no crystals; 1=some crystals, hardly visible; 2=some crystals clearly visible; 3=more than 30 crystals per well clearly visible; 4=layer of many crystals (well not fully covered); 5=layer of many crystals (well completely covered).

FIG. 15 shows Table 6: Citrate based solubility screen at 100 mg/mL husFcγRIIB and 2-8° C. The visual appearance of each formulation was assessed by light microscopy and ranked according to an arbitrary scale (0=no crystals; 1=some crystals, hardly visible; 2=some crystals clearly visible; 3=more than 30 crystals per well clearly visible; 4=layer of many crystals (well not fully covered); 5=layer of many crystals (well completely covered).

FIG. 16 shows Table 7: Citrate based solubility screen at 120 mg/mL/150 mg/mL husFcγRIIB and 2-8° C. The visual appearance of each formulation was assessed by light microscopy and ranked according to an arbitrary scale (0=no crystals; 1=some crystals, hardly visible; 2=some crystals clearly visible; 3=more than 30 crystals per well clearly visible; 4=layer of many crystals (well not fully covered); 5=layer of many crystals (well completely covered).

DESCRIPTION

Figure 1:
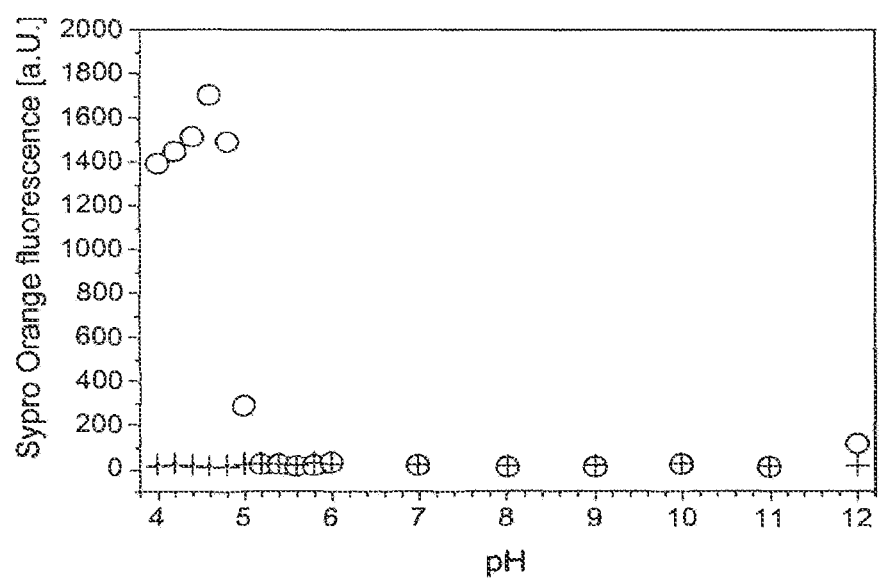
FIG. 1 depicts the determination of denaturing pH range. 0.5 mg/mL husFcγRIIB in 20 mM histidine, 150 mM NaCl (o) and blank buffer (+) were incubated at the respective pH for 3 h at room temperature. An increase in Sypro Orange fluorescence indicated the presence of denatured husFcγRIIB. husFcγRIIB did not unfold from pH 5.2 to at least pH 11.

The present invention relates to novel formulations of soluble Fc receptors and especially to formulations containing high concentrations of a soluble FcγRIIB receptor. The invention further relates to the use of such formulations as pharmaceutical compositions for the treatment of autoimmune diseases, infections, tumors and other conditions where the immune system is involved.

Human soluble FcγRIIB is a promising candidate substance for treatment of Idiopathic Thrombocytopenic Purpura, Systemic Lupus Erythematosus and other autoimmune diseases. It is one of a plurality of soluble antibody receptors which have been developed over the past 10 to 15 years.

WO 00/32767 describes soluble Fc receptors (sFcRs) which are composed of only the extracellular part of the receptor and are not glycosylated. Due to the absence of the transmembrane domain and the signal peptide, these proteins are present in a soluble form and not bound to cells as is normally the case for Fc receptors (FcRs). Furthermore the sFcRs described in WO 00/32767 can be produced recombinantly and have been suggested for the treatment of autoimmune diseases due to their ability to bind the Fc part of antibodies without interfering with other components of the immune system. WO 00/32767 additionally describes the crystal structure of certain sFcRs and the possibility of developing substances that inhibit the interaction of IgG with sFcRs with the aid of these crystal structures. The elucidation of the crystal structure enables finding such inhibitors by e.g. screening the databases using available computer programs or by computer-aided drug design.

The invention which was defined in WO 03/043648 further developed the findings of WO 00/32767 and provides treatment methods especially for diseases like multiple sclerosis (MS), systemic lupus erythematosus (SLE), and rheumatoid arthritis (RA) and also for diseases with an elevated level of natural killer (NK) cells. Even if said receptors were produced recombinantly in prokaryotes and therefore were unglycosylated, the inventors of WO 03/043648 surprisingly found that although the unglycosylated proteins were expected to be poorly soluble, the receptors could be purified with relatively high concentrations of up to 50 mg/ml of sFcγR in a soluble form.

WO 00/32767, WO 03/043648 and other publications imply an important role for FcRs in defense reactions of the immune system. When pathogens have entered the blood circulation they are bound by immunoglobulins, also known as antibodies. Since the immune response to a pathogen is polyclonal, a multitude of antibodies are produced and bind to a pathogen, leading to the formation of an immune-complex (IC). ICs are subsequently phagocytised by specialized effector cells (e.g. phagocytes or macrophages) of the immune system and thus removed from the circulation. The phagocytosis is mediated by the binding of the Fc-part of the antibodies, which, together with the pathogen, form the ICs, to FcRs on the aforementioned effector cells. Other effector cells of the immune system, such as natural killer cells, eosinophils and mast cells also carry FcRs on their surface which upon binding of ICs release stored mediators such as growth factors or toxins that support the immune response.

The FcRs of these effector cells also function as signal-transducing molecules that specifically bind immunoglobulins of various isotypes during the humoral immune response. In addition, FcRs expressed on natural killer cells play a fundamental role in the destruction of antibody-coated target cells ("antibody-dependent cell-mediated cytotoxicity", ADCC).

However, in addition to the positive effects of FcRs in the defense against pathogens, overshooting reactions caused by the presence of auto-antibodies in patients may also occur which result in an undesired stimulation of the immune system which manifests itself especially as inflammatory or autoimmune diseases. Such immune reactions directed against the body's own substances remain a major medical problem and although there are approaches for treating them, these approaches are not equally effective in every patient.

All members of the FcγR-family, i.e. FcRs which are specific for antibodies of the IgG type, are integral membrane glycoproteins, possessing extracellular domains related to a C2-set of immunoglobulin-related domains, having a single membrane spanning domain and an intracytoplasmic domain of variable length. There are three known Fcγ receptor forms, designated FcγRI (CD64), FcγRII (CD32), and FcγRIII (CD16). This invention in preferred embodiments specifically focuses on FcγRII (CD32).

FcγRII proteins are 40 KDa integral membrane glycoproteins which only bind the complexed IgG in the ICs. These receptors are the most widely expressed FcγRs, present on all hematopoietic cells, including monocytes, macrophages, B cells, NK cells, neutrophils, mast cells, and platelets. There are three human FcγRII genes (FcγRII-a, FcγRII-b, FcγRII-c), all of which bind IgG in aggregates or immune complexes.

Inflammation is a process by which the body's white blood cells react to infection by foreign substances, such as bacteria and viruses. It is usually characterized by pain, swelling, warmth and redness of the affected tissue. Effector substances known as cytokines and prostaglandins control this process, and are released in an ordered and self-limiting cascade into the blood or affected tissues. The release of such effector substances increases the blood flow to the area of injury or infection. Some of the effector substances cause a leak of fluid into the tissues, resulting in swelling. This protective process may stimulate nerves and cause pain.

These changes, when occurring for a limited period in the relevant area, work to the benefit of the body.

In autoimmune diseases the patient's immune system has lost the ability to discriminate between body-own ("self") and foreign proteins. In consequence, antibodies are generated that recognize "self"-proteins and form immune complexes which continuously activate the immune system because the "self"-protein is permanently produced and recognized as foreign. This chronic condition can persist for years leading in the end to severe organ damage and possibly to the death of the patient. There are many different autoimmune disorders which affect the body in various ways. For example, the brain is affected in individuals with multiple sclerosis, the gut is affected in individuals having Crohn's disease, and the synovium, bone and cartilage of various joints are affected in individuals suffering from rheumatoid arthritis. As autoimmune disorders progress, destruction of one or more types of body tissues, abnormal growth of an organ, or changes in organ function may result. The autoimmune disorder may affect a single organ or tissue type or may affect multiple organs and tissues. Organs and tissues commonly affected by autoimmune disorders include red blood cells, blood vessels, connective tissues, endocrine glands (e.g. the thyroid or pancreas), muscles, joints, and the skin.

Examples of inflammatory and/or autoimmune disorders include, but are not limited to, primary immune thrombocytopenia (ITP), systemic lupus erythematosus (SLE), rheumatoid arthritis (RA), autoimmune haemolytic anaemia (AIHA), diabetes, Pemphigus vulgaris, Hashimoto's thyroiditis, autoimmune inner ear disease myasthenia gravis, pernicious anemia, Addison's disease, dermatomyositis, Sjogren's syndrome, dermatomyositis, multiple sclerosis, Reiter's syndrome, Graves disease, autoimmune hepatitis, familial adenomatous polyposis and ulcerative colitis.

The FcγRs can be divided into two general classes according to their function which may be an activating or inhibitory one. The activating receptors are associated with a cytoplasmic 16 amino acid immunoreceptor tyrosine-based activation motif (ITAM) having the consensus sequence $Y-X_2-L/I-X_6-12-Y-X_2-1/L$ (Barrow and Trowsdale, EuJI, 2006, 36: 1646-1653). This motif can be found, for example, in FcγRIIA. The other class of FcRs are inhibitory receptors which contain a 6-amino acid inhibitory motif (ITIM) in the cytoplasmic part of the receptor having the consensus sequence $S/I/V/L-X-Y-X_2-I/V/L$ (Barrow and Trowsdale, EuJI, 2006, 36: 1646-1653). An example of such an inhibitory FcR is FcγRIIB.

FcγRIIB (FcγRIIB) has two inhibitory activities. One of them is dependent on the ITIM-motif and occurs when FcγRIIB is ligated to an ITAM-carrying receptor (e.g. FcγRIIA) resulting in the inhibition of ITAM-triggered calcium mobilization and cellular proliferation. The second inhibitory action of FcγRIIB involves homo-aggregation of the receptor (FcγRIIB clustering) which delivers a pro-apoptotic signal into the cytoplasm. The pro-apoptotic signal has only been reported in B-cells and can be blocked by ligation of FcγRIIB to the B-cell receptor (BCR) (JV Ravetch, S. Bolland, Annu Rev. Immunol. 2001, 19:275-90.

As mentioned above, in WO 03/043648, sFcγRIIB has already been described for use in pharmaceutical preparations where relatively high amounts of Fcγ receptors can be included in a reasonable volume of a treatment solution for e.g. injection into a patient.

Soluble Fcγ receptors and especially sFcγRIIB has been suggested for the treatment of autoimmune diseases since they can bind to antibodies but do not affect other components of the immune system. The soluble Fc receptors therefore are able to neutralize antibodies in the blood stream which has an attenuating effect especially on autoimmune processes. Possible indications that are already mentioned in WO 03/043648 include soluble Fcγ receptors for treatment of multiple sclerosis (MS), systemic lupus erythematosus (SLE) and rheumatoid arthritis (RA) and also for diseases with an elevated level of NK cells to avoid the disadvantages of the previously used treatment methods for such diseases.

The teaching of WO 03/043648 focuses on the therein discovered fact that soluble Fc receptors can be used to form aqueous solutions with a concentration of up to 50 mg/ml of soluble receptor. For certain applications such concentrations of active agent do suffice. In recent studies, however, a therapeutic dose of sFcRs like sFcγRIIB of significantly more than 1 mg/kg body weight of the patient has been established to be beneficial or even necessary for a successful treatment of autoimmune diseases.

Subcutaneous administration of pharmaceuticals is considered an effective and relatively uncomplicated and non-onerous method of delivering an active agent to a patient. Compared to intravenous infusion, which requires a more extensive medical equipment and in most cases administration at a doctor's office or a clinic, subcutaneous administration can easily be applied even by the patient himself. Subcutaneous administration will also result in a retarded onset of action, i.e. an increased half-life and time to maximal concentration. Also, it was found that the maximum plasma concentration is reduced in case of subcutaneous delivery. These effects are based on the administration beneath the skin of a patient from where the active agent is transported to the bloodstream. Proteins larger than about 16-20 kDa are generally regarded to be taken up primarily by the lymphatic system, which might be an advantage for FcγRs as the target B cell population matures and resides in the lymphatics, too (Porter, C. J. H. and Charman, S. A. (2000), J. Pharm Sci. 89, 297-310).

The subcutaneous administration route, however, is preferably limited by an injection volume of 1.0 ml up to perhaps 1.5 ml per application (Gatlin, L. A. and Gatlin, C. A. B, (1999), Gapta, P. K. & Brazeau, G. A., eds., Interpharm Press, Denver, pp. 401-425). Thus, aqueous sFcγR solutions as known from WO03/043648 could not have been considered for subcutaneous administration. Rather, for sufficiently high concentrations of receptor, precipitation and formation of undesirably large crystals of the receptors in the aqueous solution and accordingly clogging of the needles and/or pain at the injection locus had to be expected from the teaching of this document. Therefore, in spite of all the anticipated advantages, subcutaneous administration didn't seem a promising route of treatment and rather intravenous injection or infusion seemed to be the only viable delivery method.

Accordingly, it was one object of the present invention to provide means and conditions for less complicated and burdensome administration of Fc receptors to a patient and for aqueous formulations of soluble Fc receptors, especially of soluble FcγRIIB, which contain the receptor in a sufficiently high concentration to enable a subcutaneous treatment regimen for autoimmune diseases.

It was a further object of the present invention to provide such aqueous formulations of highly concentrated soluble Fc receptor in a ready-to-use form which is stable under usual storage conditions for pharmaceuticals for more than 24 months or, alternatively, in a form which allows for long-term storage and easy and straightforward adjustment and reconstitution prior to use in subcutaneous applications.

These objects were solved according to the present invention by formulations containing a soluble Fc receptor (sFcR) in an aqueous buffered solution, wherein the concentration of the Fc receptor is greater than 50 mg/ml and wherein it contains a physiologically acceptable buffer substance.

During the research which led to the present invention, it was surprisingly found that, contrary to the previous expectations, it is possible to provide soluble Fc receptors dissolved in suitable buffer solutions with a concentration of even much higher than 70 mg/ml and preferably more than 150 mg/ml, by means of which it is for the first time possible to provide sFcRs also in the form of a pharmaceutical composition for the subcutaneous application. The subcutaneous application as parenteral mode of application is simpler and faster applicable than an intravenous mode of application. As mentioned above, even the patient himself can carry out a subcutaneous application.

A short and usually thin cannula is required for subcutaneous administration. The highly concentrated formulation of the present invention provides the sFcRs in a completely dissolved and homogenous form and at acceptable viscosity that permits the use of these thin cannulas or as crystal suspension containing crystals that are small enough to pass these thin cannulas. Thus, the patients' convenience is considerably increased and an administration of the receptors can be effected by the subcutaneous route.

The inventive formulations as described in the following enable the provision of soluble FcRs and especially of soluble FcγRIIB in concentrations of up to a maximum value which is limited mainly by the increase in viscosity of the solution due to the high concentration of the Fc receptor. Upon selection of appropriate buffer substances and adjustment of suitable osmolalities, a stabilization of 220 mg/ml sFcγRIIB and more at a physiological pH is enabled within the framework of the present invention.

The physiologically acceptable buffer substances, which are used according to the present invention are commonly used buffers for the pharmaceutical application of suitable solutions. Within the framework of the present invention, however, it was found that depending on the buffer substance used, the pH value of the solution has a considerable influence on the solubility of the Fc receptors. Depending on the buffer chosen, the pH value has to be adjusted within a determined range and especially to a particular optimum for achieving the desired solubility of the Fc receptors, especially if the purpose is to provide a formulation which does not contain any crystalline sFcR.

It was further found that the protein itself is able to sufficiently act as a buffer due to the presence of positively and negatively charged amino acids. Thus, e.g. by selecting an appropriate pH value based on the pK-value of the proteins amino acid side chains, it is possible to forgo the addition of a separate buffer substance as long as a suitable amount of protein is present in the solution to act as the physiologically acceptable buffer substance.

In preferred embodiments of the present invention, as a buffer substance, the formulation contains one of a histidine buffer, citrate buffer or phosphate buffer. However, it is particularly preferred to prepare the formulation with either a histidine or a citrate buffer.

In both cases, it was found that the adjustment of the pH value in these buffered solutions permits an adaption of the solubility of the Fc receptors by means of which high concentrations of Fc receptor can be dissolved, however, can also be caused to crystallize by means of increasing or decreasing the pH value depending on the buffer substance used. This possibility of changing between soluble and crystalline forms of sFcR by the mere adaption of the pH value implies considerable advantages in view of adaptations with regard to the applicability, preservation and storage stability of pharmaceutical compositions.

For example, during marketing authorization procedures, sufficient storage stabilities of pharmaceuticals have to be proven. In this context, it is essential that stability data of a storage of at least 12 months at a temperature of 5° C. be included by the party requesting the marketing authorization. However, it is desirable and advantageous that a storage stability for more than 24 months under corresponding conditions is achieved, whereby in view of the mentioned storage conditions, a substantial amount, preferably 90% of the pharmaceutical agent still needs to be present in an active form after the expiration of the time.

In this context, the inventive formulations show particular advantages. For instance, they allow to offer highly concentrated sFcR formulations in liquid form which exclusively contain dissolved Fc receptor and which show a high storage stability.

Moreover, the inventive formulations can be subjected to lyophilization to provide a solid storage form. Such solid forms might even show improved storage stability as compared to the liquid formulations. Such formulations are therefore a further subject matter of the present invention.

Lyophilisation can be performed in any suitable manner known to the skilled person for lyophilising proteins. Preferably, conditions as mild as possible are used to avoid protein degradation.

From the solid form, ready-to-use liquid formulations can easily be restored by the addition of water for injection, saline or buffered aqeuous solutions to provide the Fc receptor again in completely dissolved form or intermediate steps can be chosen in which the solubility is adapted as desired.

Also concentrated forms of inventive formulations are a further subject matter of the present invention. Such concentrated forms can be obtained by e.g. removing part of the liquid to below the solubility limit which results in formulations containing at least some crystalline receptors. Also from such formulations, the sFcR can be reconstituted to a ready-to-use liquid formulation by adding water for injection, saline or buffered aqeuous solutions to the desired concentration of active sFcR and especially to concentrations in which the sFcR is present entirely in dissolved form.

Due to the pH dependency of the solubility of Fc receptor in the formulations according to the present invention, the formulations provide the additional advantage that the Fc receptor can practically be caused to crystallize entirely by means of adapting the pH and can be obtained (e.g. after sedimentation or centrifugation) as concentrated crystal suspension. The crystals obtainable thereby can be very small (microcrystals), especially depending on the crystallisation conditions. The faster the crystallisation, the smaller the crystals are. Contrary to prior art, the present invention permits the fast and nearly quantitative transformation of solubilised sFcR into protein microcrystals and vice versa and thus allows to tailor the solubility properties of respective solutions and formulations. This is a further possibility to ensure excellent storage stability and in particular the need for only little storage space for an active agent, which can then be converted into an entirely or mainly soluble form by means of dissolution in a suitable buffered aqueous solution having a suitable pH value. This can, for instance, be done immediately prior to its application as a pharmaceutical by means of admixing concentrated crystal suspension with a suitable buffer. Alternatively a microcrystalline suspension or formulation might be directly administered by subcutaneous application as the present invention provides means to transform the receptor into microcrystals, i.e. crystals that are small enough to pass a cannula or thin needle. Compared to highly concentrated liquid formulations, the viscosity of such microcrystal suspensions is much lower and does not rise exponentially with increasing protein concentration.

For the purposes of the present invention and as used above in the context of describing the present invention, Fc receptors are considered as "crystalline" when crystals have an average size of more than 500 µm in diameter, whereas microcrystalline forms contain microcrystals with a size of equal to or less than 500 µm in diameter.

The present invention enables in an unprecedented way to provide soluble Fc receptors in high concentrations in different forms suitable for immediate or future pharmaceutical use. As illustrated above, this can be effected in a ready-to-use dissolved form or in a solid, e.g. lyophilized form obtained from such solution or in microcrystalline form precipitated by pH value adaption, which can then be reconstituted by resolubilization so that a formulation results in which the Fc receptor is contained in high concentration in a suitable buffer solution at the desired pH value.

In preferred embodiments of the present invention, the inventive formulation contains as an Fc receptor a sFcγ receptor. Regarding the possibility of treating autoimmune diseases, the sFcγRII receptors and especially sFcγRIIB have to be considered. A particularly preferred inventive formulation thus contains the soluble FcγRIIB receptor in a pharmaceutically applicable solution with a suitable buffer substance.

For the purposes of the present invention, the FcγRIIB receptor has a sequence as described in the prior art, especially WO 00/32767 and WO 03/043648 or other documents referring especially to FcγRIIB and especially sFcγRIIB. Further, the term is meant to encompass forms of the receptor which can differ especially in their N-terminal parts. An especially preferred sFcγRIIB protein is shown in SEQ ID NO:1. This sequence contains a methionine residue at the N-terminus, which is e.g. required for prokaryotic expression, however is cleaved off in a major part of the produced proteins by bacterial mechanisms later on. Therefore proteins according to SEQ ID NO:1 lacking the N-terminal methionine are also encompassed within the present invention as well as mixtures of proteins with and without the N-terminal Met. Further, depending on the production process and the condition of the bacterial production strain, additional changes in the N-terminal five amino acids can occur. E.g. in addition to methionine also the following residues can be cleaved off or methionine could be exchanged for another amino acid like norleucine. Therefore also mixtures of all these proteins differing at the N-terminus and originating from production processes using a DNA sequence which encodes for the amino acid sequence of SEQ ID NO:1 are encompassed by the current definition of sFcγRIIB and especially by the term husFcγRIIB.

In further preferred embodiments, FcγRIIB proteins are considered as encompassed by the present invention as long as they have an at least 90% identity to the protein of SEQ ID NO:1. For the determination of sequence identity a comparison is made by aligning the sequences in a manner to provide the maximum correspondence of amino acids. It is especially preferred that differences in the claimed proteins occur only within the first ten and most preferably within the first five amino acids. It is especially preferred that the proteins have an amino acid identity of at least 95% with differences occurring within the first five amino acids of SEQ ID NO:1, wherein the differences in the amino acids are based on at least one of deletions, substitutions and additions.

In a particularly preferred embodiment, this formulation according to the present invention contains the sFc receptor and especially the sFcγRIIB receptor in concentrations of greater than 60 mg/ml, more preferably greater than 60-80 mg/ml, still more preferably greater than 80 mg/ml, even more preferably greater than 100 mg/ml and particularly preferred greater than 150 mg/ml and most preferably even greater than 200 mg/ml.

The inventive formulations optionally contain further pharmaceutically acceptable substances, which are for example used for the adjustment of the ionic strength of the solution and/or promote the solubility and stability of the receptor protein contained therein. Such substances are known to the skilled person. For the adjustment of the ionic strength the inventive formulation optionally contains a salt and preferably NaCl. For the stabilization of the protein, polyols and especially sugars and sugar alcohols like sucrose or mannitol can be used. Further, the inventive formulation preferably contains detergents which are suitable for pharmaceutical applications, as for example polysorbates.

Buffer substances are preferably contained in the formulation of the present invention in an amount of 0.1 µM to 300 mM. In more preferred embodiments, the physiologically acceptable buffer is present in an amount of 0.1 to 150 mM and especially 1 to 50 mM.

For the adjustment of the osmolality (isotonicity), salts like sodium chloride are suitable in such amounts which adjust a preferably physiological osmolality, at least as far as the formulation is intended for the direct administration to a patient. The osmolality of the solution can be adjusted over a wide range and can be set to between 10 mOsm/kg and greater than 600 mOsm/kg without having a considerable effect on the solubility of the Fc receptor.

Salt, preferably NaCl, is present in the formulation in a concentration of about 0 to 250 mM, preferably 5 to 200 mM and most preferably 10 to 50 mM.

Polyols like sucrose are not necessarily contained in the inventive formulations, however in preferred embodiments they are present in an amount of at least 1.0% and more preferred at least 2.0%. The preferred upper limit of the amount of polyols is approximately 25%, more preferably 15% and most preferably 8%. Sugars are known to stabilize proteins in solution.

Salts and sugars need to be balanced to adapt the osmolality of the formulation, preferably to be isotonic. The more sugar is contained in the formulation, the less salt can be added and vice versa.

Suitable amounts of detergents, which are preferably used within the context of the invention, are 0.001-0.1%, particularly 0.005-0.05%.

As already mentioned above, the findings, which have been obtained within the framework of the present invention, allow the adaption of the solubility conditions for soluble Fc receptors and especially sFcγRIIB in such a way that for a content of Fc receptor of greater than 50 mg/ml, a predetermined provision of the receptors is made possible in either completely dissolved form or in a microcrystalline form for administration to a patient. As also mentioned above, it is often advantageous for an administration to a patient to provide as high a concentration as possible in a completely dissolved form or at least transformable into a dissolved form.

For formulations containing microcrystalline sFcRs, an administration to the patient may also be possible, whereby the microcrystals completely dissolve after administration and the active substance is available with its physiologic effect. For other administrations and also for storage, it can be of advantage to rather keep the receptor in crystalline form, wherein it is especially stable against degradation and thus loss of activity.

Accordingly, preferred embodiments of the present invention are formulations, which are completely liquid and wherein the receptor is present in solubilized form or in suitable microcrystalline form An especially preferred formulation of the present invention contains the soluble FcγRIIB receptor in a citrate buffered solution and possesses a pH value of equal to or greater than 6. The pH value is preferably adjusted within a range of 6.0-7.5. In such citrate buffered solutions with a physiological pH value, the FcγRIIB receptor is soluble in concentrations of greater than 140 mg/ml. Due to the physiological pH value, such formulation also has the advantage that it can directly be administered to a patient without causing side effects like pain at the site of administration.

In another preferred embodiment, the soluble FcγRIIB receptor is contained in a histidine buffered solution with a pH value of 5.2-5.9. When using a histidine buffer, sFcγRIIB is soluble in concentrations of more than 100 mg/ml.

At a pH of approximately 6.0, the solubility of the receptor is still relatively high, however, crystalline precipitates are beginning to form whereas at a higher pH, only a substantially lower solubility of the receptor is observed.

Both formulations described above enable a high concentration of solubilized sFcγRIIB receptor, whereby this could be shown for both the mentioned citrate buffered formulation and for the histidine buffered formulation up to the viscosity limited regimen of approximately 220 mg/ml (see enclosed examples).

The inventive formulations further have excellent freeze/thaw stability properties and also excellent stabilities at reduced temperatures of 2° C.-8° C. Even the stability at room temperature is excellent for these solutions.

The usability of both solutions is both given for a direct administration to the patient and in the production of a lyophilized or highly concentrated formulation that can contain crystals and is convenient for storing or generation of injection solutions which are directly reconstitutable by the patient.

For the direct administration, as already mentioned above, the citrate buffered solution with a physiological pH value is particularly preferred.

A particularly preferred further subject of the invention is a formulation which contains the receptor in crystalline form. Such formulations are preferably embodied as a citrate buffered suspension with a pH value of 5.2-5.9 or alternatively as a histidine buffered suspension at a pH value of 6.0-7.5. Such suspensions can for example preferably be used as storage-stable forms which, for the administration to the patient, can be transformed to a formulation containing high concentrations of the solubilized receptor by means of pH adjustment. Additionally, the same can also be concentrated or the receptor be obtained from them by separation of the solution in order to obtain a highly concentrated crystal suspension. The receptor can be recovered in completely dissolved form by reconstitution in a suitable buffer at a suitable pH value.

The described inventive formulations and the finding that, using certain buffer substances, depending on the pH value different solubility levels of Fc receptors can be realized enable on the one hand the provision of ready-to-use injections for the subcutaneous administration to a patient, or on the other hand the provision of particularly storage-stable variants containing crystalline Fc receptor. Even lyophilized or otherwise solid forms of the receptor are provided which can be transformed by a simple addition of the suitable solutions into ready-to-use forms containing high concentrations of soluble receptor.

A further subject of the present invention is thus a pharmaceutical composition, which comprises a formulation according to the present invention as described above and in which further pharmaceutically acceptable excipients and/or adjuvants and/or carriers can be present. In particularly preferred embodiments these pharmaceutical compositions are directly applicable for the subcutaneous injection of an effective amount of a soluble Fc receptor and especially for the treatment of autoimmune diseases.

In one preferred embodiment, the pharmaceutical composition preferably contains a sufficient amount of completely dissolved sFc receptor in a suitable buffer substance and at a physiological pH value. Such pharmaceutical composition is a ready-to-use medicament and can be directly applied to the patient. The dissolved soluble receptor can e.g. easily be absorbed into the patient's lymphatic circulation and be directly effective there or after transport within the patient's body by blood or body fluid circulation.

Alternatively, the pharmaceutical composition can contain the receptor in a highly concentrated and at least partially microcrystalline or crystalline form. Diluted as necessary with suitable buffer solutions, the pharmaceutical composition is again particularly suitable for the subcutaneous injection of an effective amount of Fc receptors.

As already explained above in the context of describing the present invention, Fc receptors are considered as "crystalline" when crystals have an average size of more than 500 μm in diameter, whereas microcrystalline forms contain crystals with a size of equal to or less than 500 μm in diameter. As far as a direct application to the patient is considered, pharmaceutical compositions containing completely dissolved Fc receptor can of course be used but also pharmaceutical compositions containing formulations with the Fc receptor being solely or partially in microcrystalline form have merit in pharmaceutical applications. These microcrystals are small enough to not clog the needles for subcutaneous application. The use of microcrystals-containing solutions can be beneficial for e.g. delayed or sustained release of the active sFc receptor to the patient's system and, under certain circumstances, such microcrystalline forms can even be considered as preferred pharmaceutical compositions.

Pharmaceutical compositions of the present invention containing microcrystalline or crystalline forms of Fc receptors can e.g. be obtained by concentration of the sFc beyond its solubility by conventional concentration techniques like ultrafiltration. It is possible to maintain the pharmaceutical in liquid form containing a certain amount of crystals or microcrystals. Instead of using a mechanical concentration method for obtaining crystals or microcrystals, it is also possible and a preferred embodiment of the present invention to crystallize the receptor by adjusting the pH to a value wherein the receptor has a considerably lower solubility. The precipitated crystals or microcrystals can be separated from the solution and used for storage and subsequent reconstitution or direct administration. The solid forms of receptor formulations are especially storage stable and maintain their effectiveness for at least more than 24 months.

In such cases, the pharmaceutical composition is conveniently provided in a pharmaceutical kit format, which in addition to the solid or highly concentrated sFcR also comprises the suitable liquid for the reconstitution of an injectable solution. A further subject matter of the present invention is therefore a pharmaceutical kit containing crystalline or lyophilized soluble Fc receptor and a suitable pharmaceutically acceptable liquid like buffer solution or simply water for the reconstitution of the injection solution in suitable separate storage units.

It is especially preferred for an inventive pharmaceutical kit, if sFcR receptor and buffer solution for the reconstitution of the injection solution are provided in suitable devices for simple mixing and well protected against contamination. Preferably, the kit contains a buffer solution based on a phosphate buffer, a histidine buffer or a citrate buffer. It is further preferred for the buffer solutions that the pH is adapted to provide optimum solubility for the Fc receptor. In especially preferred embodiments of the present invention, the buffer solution is a citrate buffered solution with a pH of above 6, especially 6.1 to 7.5, or a histidine buffered solution with a pH of below 6.0, especially 5.2 to 5.9. The citrate buffered solution is the most preferred buffer contained in a pharmaceutical kit according to the present invention.

The amount of buffered solution contained within the pharmaceutical kit is adapted to the amount of solid or concentrated sFcR in the kit. Depending on whether a complete dissolution of the sFc receptor or maintaining some amount of microcrystals is desired, a corresponding buffer is selected in a suitable amount of liquid and also the pH of the solution is adapted according to the teaching concerning sFcR solubility as provided herein.

A further subject matter of the present invention is the use of the formulations, the pharmaceutical compositions and pharmaceutical kits of the present invention for the prevention or treatment of autoimmune diseases. More particularly, the present invention is intended for the use within the framework of the prevention or treatment of multiple sclerosis, systemic lupus erythematosus, rheumatoid arthritis, primary immune thrombocytopenia and autoimmune haemolytic anemia (AIHA). Further, the formulations, pharmaceutical agents and pharmaceutical kits can be used for the treatment of inflammatory disorders. The inventive subject matter enable the application of Fc receptors for all indications for which these have already been described or for which they are considered to be suitable in the future. The inventive formulations and pharmaceutical compositions and kits allow especially the subcutaneous administration which is very efficient and easily applicable to (or by) a patient. The possibility of administering especially high amounts and concentrations of Fc receptors is a particular advantage of the present invention.

The following examples shall further explain the invention and its advantageous effects and embodiments.

Example: Development of High Concentrated Liquid husFcγRIIb Formulations Suitable for Subcutaneous Delivery 1. Materials The following solutions of husFcγRIIB (soluble human FcγRIIB receptor having the amino acid sequence as shown in SEQ ID NO. 1) were used as parent material for all experiments:

a) husFcγRIIB 5 mg/ml concentrate for solution for infusion
  5 mg/mL husFcγRIIB in 5.3 mM $NaH_2PO_4$, 1.94 mM $KH_2PO_4$, 150 mM NaCl, 2% (w/v) mannitol, 0.005% polysorbate 20 pH 6.5
b) husFcγRIIB 20 mg/mL concentrate for solution for infusion
  20 mg/mL husFcγRIIB in 20 mM histidine, 150 mM NaCl, 2% (w/v) sucrose, 1% (w/v) mannitol, 0.005% polysorbate 20 pH 6.5.

The following chemicals of at least the indicated grades were used:

| Name | Purity | Supplier |
| --- | --- | --- |
| Citric acid monohydrate | p.a. | Merck |
| Sodium hydroxide | Ph. Eur. (≥98%) | Carl Roth |
| Sodium chloride | Ph. Eur. (≥99%) | Carl Roth |
| Ethanol, abs. | Ph. Eur. (≥99.8%) | Carl Roth |
| Histidine | Ph. Eur. (≥98.5%) | Carl Roth |
| Hydrochloric acid, 37% | p.a. | Carl Roth |
| Sucrose | Ph. Eur. (≥99%) | Carl Roth |
| Mannitol | ACS reagent (≥99%) | Fluka |
| Polysorbate 20 (Tween 20) | cell culture tested | Sigma Aldrich |
| Trehalose | for biochemistry | Merck |

2. Methods a) husFcγRIIB Content by UV/Vis Spectroscopy

The sample was transferred to a UV micro-cuvette (UV cuvette micro, Plastibrand, Brand) and the absorbance was measured with a Spectrophotometer (Cary 100, Varian) using the respective buffer as blank.

The husFcγRIIB concentration was calculated by the following equation:

$$\text{husFcγRIIBconc. [mg/mL]} = (A_{280} - A_{320}) \times DF \times 0.64$$

DF=dilution factor b) husFcγRIIB Buffer Exchange by Cation Exchange Chromatography 1000-1800 mg husFcγRIIB (husFcγRIIB 5 mg/mL concentrate for solution for Infusion) was carefully diluted with 10 mM citrate/NaOH pH 6.5 until the conductivity reached 5.0±0.1 mS/cm. The diluted protein was filtered (0.2 μm Durapore membrane PVDF hydrophil, 47 mm, Millipore) and loaded at 5.5 mL/min onto a 57 mL SP Sepharose HP cation exchange (CEX) resin (26×107 mm, GE Healthcare; equals 17.5-31.6 mg husFcγRIIB/mL resin) equilibrated in 10 mM citrate/NaOH, 20 mM NaCl pH 6.5. Bound protein was washed at 5.5 mL/min with 200 mL 10 mM citrate/NaOH, 20 mM NaCl pH 6.5 and eluted with a 300 mL linear gradient ranging from 20 mM to 600 mM NaCl in 10 mM citrate/NaOH pH 6.5. Eluate collection was started after $OD_{280}$ exceeded 250 mAU (AU: adsorbance units) and was stopped after it dropped below 200 mAU (1 cm path length, Akta Explorer 100, GE Healthcare). The column was regenerated with 100 mL 1 M NaCl, washed with 150 mL MilliQ $H_2O$ (ultrapure water, Millipore Corp.) and stored until further use in 20% ethanol. After husFcγRIIB content measurement by UV/Vis spectroscopy the eluate was filtered (Millex 33 mm, 0.2 μm Durapore PVDF (polyvinyliden fluoride) hydrophil, both from Millipore Corp.), aliquoted, snap-frozen in liquid nitrogen and stored at ≤−70° C. until use.

The NaCl content was calculated by correlation of the mean conductivity of the eluate to the measured conductivity at 10 mM citrate/NaOH, 20 mM NaCl and 10 mM citrate/NaOH, 600 mM NaCl.

Histidine buffered husFcγRIIB was prepared similarly using 10 mM histidine/HCl as buffering species.

c) pH Stability Screen

A concentrated husFcγRIIB solution in 20 mM histidine, 324 mM NaCl pH 6.5 was adjusted to 0.5 mg/mL husFcγRIIB, 20 mM histidine, 150 mM NaCl, 2.5× Sypro Orange (5000× in DMSO, Molecular Probes™, Invitrogen) using suitable stock solutions. The pH of the solution was adjusted between pH 4 and pH 12 based on an experimental titration curve with 0.2 M HCl or 0.2 M NaOH. 40 µL of the solution were incubated in a sealed 96 well half area well plate (µclear, black, medium binding; Greiner BioOne) for 3 h at 25° C. and assayed for Sypro Orange fluorescence (Excitation 485 nm, Emission 590 nm, gain 60, lag time 0 µs, integration time 40 µs; TECAN Spectrofluor plus).

d) Preparation of High Concentrated Formulations

The required NaCl content of histidine or citrate buffered husFcγRIIB (initial concentration approx. 200-300 mM NaCl) was adjusted by dilution with the appropriate buffer (10 mM citrate or 10 mM histidine pH 6.5) and subsequent ultrafiltration (Vivaspin 20, 5 kDa MWCO, Sartorius). In order to keep the processed volumes small, the procedure was repeated for up to 3 cycles in total. After final dilution, the pH was measured (pH-meter H18314, pH-electrode H11217, Hanna instruments), adjusted with 0.2 M NaOH or 0.2 M HCl in the appropriate buffer and the protein solution was concentrated. The husFcγRIIB content was measured by means of UV/Vis spectroscopy in triplicate, the husFcγRIIB concentration was adjusted with the appropriate buffer and the solution was filtered (Ultrafree MC, 0.2 µm Durapore PVDF hydrophil, Millipore).

e) husFcγRIIB Solubility Screens in 384 Well Format

The solubility of high concentrated husFcγRIIB solutions in relation to buffering species, pH, salt concentration and sugar/polyol concentration was assessed in 384 well format (µclear, white, non-binding, Greiner BioOne) using 30 µL per well. The final formulations were prepared by direct addition of filtered stock solutions to each well. The following stock solutions were used: 100-195 mg/mL husFcγRIIB, 1.5 M NaCl and 30% (w/v) sucrose+15% (w/v) mannitol in either 10 mM citrate pH 7.0 or 10 mM histidine pH 5.5. Each solution was supplied with 0.01% (w/w) polysorbat 20 and depending with the screen with 10-50 mM NaCl.

The pH of each well was adjusted with 0.5 M-0.75 M HCl or NaOH. The required amount of acid or base was calculated based on theoretical titration curves assuming that all nine histidine residues of husFcγRIIB (pKa=6.00) provide additional buffering capacity. The plate was centrifuged (500·g, 1 min), sealed with adhesive tape (microtest tape, permacel, neo-lab) and stored at 5±3° C. in the dark.

The visual appearance of each formulation was assessed by light microscopy (Axiovert 25f, Carl Zeiss) and ranked according to an arbitrary scale (0=no crystals; 1=some crystals, hardly visible; 2=some crystals clearly visible; 3=more than 30 crystals per well clearly visible; 4=incomplete layer of many crystals (well not fully covered); 5=full layer of many crystals (well completely covered).

Taken into account dissolved salt, sugar and protein the osmolality of each formulation was calculated according to the following equation:

$$\xi_m = \sum_i v_i m_i F_{m,i}$$

wherein $v_i$ is the number of particles formed by the dissociation of one molecule of the $i^{th}$ solute and $m_i$ is the molality of the $i^{th}$ solute. For simplicity the molal osmotic coefficient $F_{m,i}$ for each solute was assumed to be equal to 1.

f) Small Scale Crystallization of husFcγRIIB

10 µL-450 µL husFcγRIIB at 50-140 mg/mL in 10 mM histidine, 10 mM NaCl, 0.01% polysorbate 20, pH 5.5 were diluted with appropriate diluents to 40 mg/mL husFcγRIIB in 10 mM histidine, 10 mM NaCl, 0.01% polysorbate 20 in a 1.5 mL polypropylene reaction tube. The pH was adjusted to 6.5-7.2 by the addition of 4.38-6.23 Vol % (final volume after addition of diluents) 0.3 M NaOH. The required amount of acid or base was calculated based on theoretical titration curves assuming that all nine histidine residues of husFcγRIIB (pK=6.00) provide additional buffering capacity.

g) Differential Scanning Fluorometry

120 µL of each formulation containing 0.5 mg/mL husFcγRIIB were prepared in a 1.5 mL test tube similarly to the procedure described above in 2.e). Sypro Orange (5000× in DMSO, Molecular Probes™, Invitrogen) was added to a final concentration of 2.5× using a 200× stock in the appropriate buffer. 30 µL of each formulation were transferred in triplicate to a well plate (MicroAmp 96 well optical reaction plate, Applied Biosystems) and the plate was sealed with adhesive tape (MicroAmp optical adhesive film, Applied Biosystems). The plate was subjected to a temperature ramp from 19° C. to 90° C. with a slope of 1° C./min and the fluorescence emission at 610 nm was recorded (7300 Real Time PCR system, Applied Biosystems). The fluorescence was differentiated with respect to time, a spline was calculated and the first detected maximum was reported as the melting temperature of husFcγRIIB (Origin 8.0, OriginLab).

h) Turbidity Screen in 384 Well Format husFcγRIIB formulations were prepared in a 1.5 mL test tube similarly to the procedure described above in 2.3). 30 µL of each formulation were transferred in duplicate to a 384 well plate (µclear, white, non-binding, Greiner), the plate was sealed with adhesive tape (microtest tape, permacel, neo-lab) and placed in an incubator. As control the respective placebo solutions were prepared. The turbidity was measured at 360 nm (Spectrafluor, bandpass filter 360/35 nm, 3 flashes, Tecan). To avoid corrupted measurements due to the condensation of water, the plate reader was pre-heated to the assay temperature.

i) Dynamic Viscosity by Pressure Drop Measurement

The dynamic viscosity of husFcγRIIB containing formulations was determined by measuring the pressure drop as liquid flows through a flow channel (m-Vroc, Rheosense). For each measurement 100 µL containing formulation was filled with a 200 µL pipette into the cylinder of a 100 µL gastight syringe (Hamilton). The syringe was installed into the rheometer and 80 µL were injected at a flow rate of 50 µL/min and 20° C.

j) Quantitative Polysorbat 20 Assay

The polysorbate content was determined by a modified protocol which is based on the colorimetric assay first described by Brown and Hayes, (1955) Analyst 80, 755-767. 500 µL of the solution to be analysed were extracted three times with 500 µL ethylacetate in a 1.5 mL polypropylene tube (VWR). To accelerate the phase separation, the tube was centrifuged (20'000·g, 5 min, 25° C.). The organic supernatants were combined in a HPLC vial (ND9, screw threaded, with conical bottom and PTFE screw cap, VWR) and the solvent was evaporated (25° C., 10 mbar, 0.5 h-1 h). The residual solids were suspended in 800 µL reagent solution (100 mM Co(NO$_3$)$_2$, 2.63 M NHaSCN in water) and were extracted with 150 µL CHCl$_3$. 100 µL of the CHCl$_3$ extract were transferred to a quartz UV micro cuvette (Hellma), the spectrum was measured from 200-800 nm (8453 diode array spectrophotometer, Agilent) and the absorbance at 620 nm corrected by the absorbance at 530 nm was recorded. As blank an extract of an equivalent solution containing no polysorbate 20 was used. Each sample was prepared in duplicate. The polysorbate 20 content was determined based on a standard curve from 0 to 0.006% (w/w) polysorbate 20 in the respective buffer.

k) Lyophilisation 59 formulations containing 15-120 mg/mL husFcγRIIB in 5 mM citrate, 10-25 mM NaCl, 2-8% (w/v) sucrose, trehalose or mannitol and 0.005-0.01% (w/v) polysorbate 20 were prepared and 400 μL were filled into 1.5 mL clear HPLC vials (32×11.6 mm, wide opening, VWR). The vials were subjected to a conservative lyophilisation cycle using the freeze-drier Epsilon 2-12D FD02 (Martin Christ, Osterrode, Germany). The vacuum during the freeze-drying process was controlled by a MKS Capacitance Manometer. The samples were frozen at −45° C., primary drying was performed for 15 h at 45° C. to 15° C., 0.12 mbar and secondary drying was performed for 10 h at 15° C. to 20° C., 0.12 mbar. The lyophilisate was reconstituted in 100-400 μL water for injection. The solution was analyzed in respect to the formation of particulates by visual inspection, turbidity measurement and fluorescence microscopy. In brief, for fluorescence microscopic examination 50 μL of the husFcγRIIB containing solution was placed into a 384 well plate (μclear, white, non-binding, Greiner) and mixed with 5 μL 25× Sypro Orange (5000× in DMSO, Molecular Probes™, Invitrogen) in 5 mM citrate, 10 mM NaCl pH 6.7. The plate was incubated for 10 min at 25° C., centrifuged (1'000·g, 3 min) and the appearance of each formulation was assessed by fluorescence microscopy (Axiovert 25f, excitation filter 470/20 nm, dichroic 493 nm, emission filter 503-530 nm, Carl Zeiss).

3. Results a) Definition of pH Range and Buffering Species for High Concentrated husFcγRIIB Solutions The husFcγRIIB denaturing pH range was determined using Sypro Orange as an indicator for the presence of unfolded protein. Sypro Orange is an environment sensitive dye whose fluorescence emission is strongly increased after its binding to hydrophobic structures (Layton & Hellinga, 2010, Biochemistry 49 (51), 10831-10841). FIG. 1 shows the results of experiments to determine the denaturing pH range. Therefore, 0.5 mg/mL husFcγRIIB in 20 mM histidine, 150 mM NaCl (o) and blank buffer (+) were incubated at the respective pH for 3 h at room temperature. An increase in Sypro Orange fluorescence indicated the presence of denatured husFcγRIIB. As shown in FIG. 1, husFcγRIIB did not unfold from pH 5.2 to at least pH 11.

To prevent pain during subcutaneous administration the administered solution should have a pH in the physiologic range. Typical buffering species that buffer in this range and are generally regarded as safe include histidine (pka~6.0), citrate ($pKa_3$~6.4) and phosphate ($pKa2$~7.2). Due to its tendency to promote pH shifts during freeze/thaw (MacKenzie, 1977) phosphate was not included in subsequent solubility screens.

In an initial attempt to determine the limiting husFcγRIIB concentration in respect to protein precipitation husFcγRIIB was concentrated by ultrafiltration in the presence of 10 mM histidine or 10 mM citrate and 10 mM NaCl until a visible precipitate was formed. As shown in Table 1 histidine buffered husFcγRIIB showed increased solubility in the slightly acidic range from pH 5.5 to 6.0 whereas citrate as buffering species provided solubility in the near neutral pH range around pH 6.5. In summary the husFcγRIIB solubility at various pH is largely dependent on the buffering species used. By microscopy it was shown that the precipitate is composed of crystalline needles.

TABLE 1 husFcγRIIB solubility limit (in mg/mL) in 10 mM histidine or 10 mM citrate at low ionic strength from pH 5.5 to 7.5. husFcγRIIB was concentrated by ultrafiltration until the solution became cloudy. Histidine buffered husFcγRIIB precipitated at pH 6.0, 6.5 and 7.0 whereas citrate buffered husFcγRIIB precipitated at pH 5.5 and pH 6.0. The sediment was identified as husFcγRIIB protein crystals.

| | pH | | | |
|---|---|---|---|---|
| | 5.5 | 6.0 | 6.5 | 7.0 |
| Histidine | >162 | ≤174 | ≤40 | ≤10 |
| Citrate | ≤40 | ≤158 | >154 | >148 |

Crystallization of husFcγRIIB

Figure 2A:
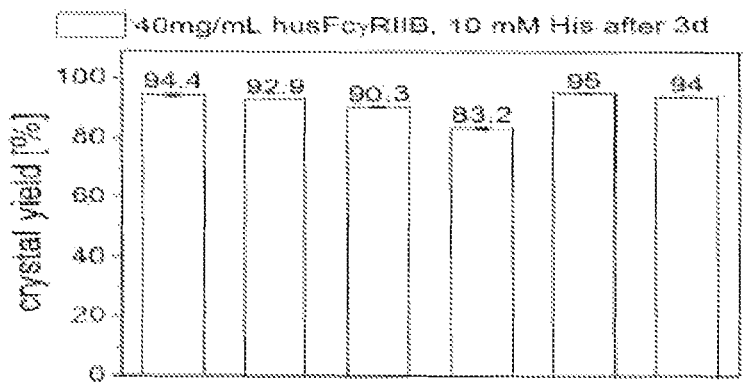
FIGS. 2A and 2B depicts the crystallization of husFcγRIIB. husFcγRIIB crystallization in 10 mM histidine pH 6.7 (FIG. 2A) or 10 mM citrate pH 5.5 (FIG. 2B) as a function of NaCl and sugar (2:1 sucrose:mannitol) concentration. husFcγRIIB crystallizes more readily and the crystal yield is much higher in the presence of 10 mM histidine, 10 mM NaCl pH 6.7 compared to 10 mM citrate, 10 mM NaCl pH 5.5.
Figure 2B:
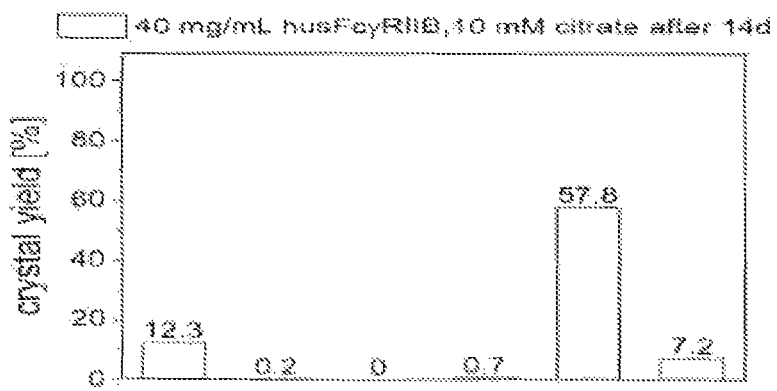

Histidine buffered husFcγRIIB remains soluble above 100 mg/mL at pH 5.5 and can be crystallized by neutralization at low ionic strength, on the contrary citrate buffered husFcγRIIB remains soluble at neutral pH above 100 mg/mL and can be crystallized by mild acidification at low ionic strength (Table 1). In a further test, crystallisation of husFcγRIIB was investigated in dependence of the presence and the amount of sugar and NaCl in the buffer. husFcγRIIB crystallisation was performed in 10 mM histidine pH 6.7 (FIG. 2a) or 10 mM citrate pH 5.5 (FIG. 2b) as a function of NaCl and sugar (2:1 sucrose:mannitol) concentration. husFcγRIIB in 10 mM histidine, 10 mM NaCl pH 5.5 or 10 mM citrate, 10 mM NaCl pH 7.0, respectively, was concentrated to 140 mg/mL by ultrafiltration and diluted to 40 mg/mL with appropriate stock solutions. In case of histidine buffered husFcγRIIB, the crystal yield was determined by measuring the husFcγRIIB concentration in the supernatant after 3 d at 2-8° C. In case of citrate buffered husFcγRIIB, no crystal growth was detected until day 10. Therefore, the crystal yield was determined after 14 d at 2.8° C. Each solution contained 0.01% polysorbate 20.

FIG. 2 shows that husFcγRIIB crystallizes more readily and the crystal yield is much higher in the presence of 10 mM histidine, 10 mM NaCl pH 6.7 compared to 10 mM citrate, 10 mM NaCl pH 5.5. Further reduction of the sodium chloride concentration from 10 mM to 5 mM resulted in a marginal increase in crystal yield when using histidine as buffering species but showed a strong effect when using citrate buffer. Reduction of the salt concentration below 5 mM and/or reduction of pH might further stimulate the crystallization process in the presence of citrate. Increased NaCl concentrations or the addition of polyols, e.g. sucrose or mannitol, above 5% inhibited the crystallization process.

Figure 3:
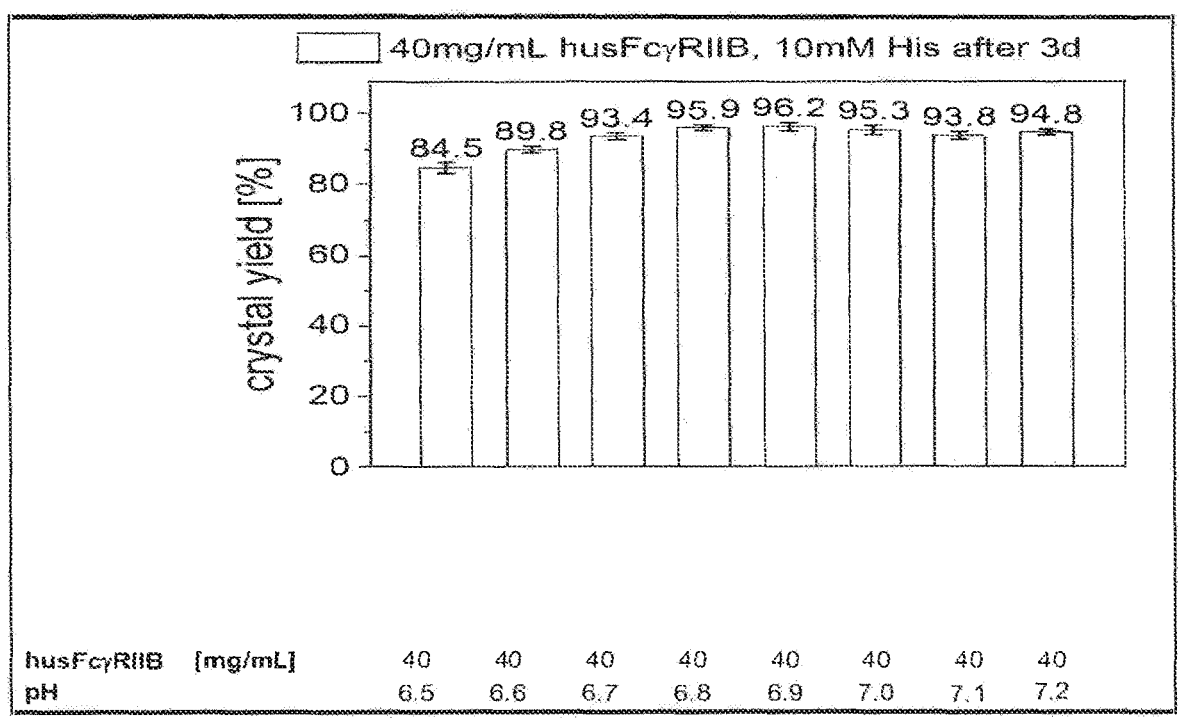
FIG. 3 depicts husFcγRIIB crystallization performed in 10 mM histidine, 10 mM NaCl as a function of pH. husFcγRIIB in 10 mM histidine, 10 mM NaCl pH 5.5 was concentrated to 140 mg/mL by ultrafiltration and diluted to 40 mg/mL with appropriate stock solutions. The crystal yield was determined by measuring the husFcγRIIB concentration in the supernatant after 3 d at 2.8$^{t\circ}$ C. Each solution contained 0.01% polysorbate 20.
Figure 4A:
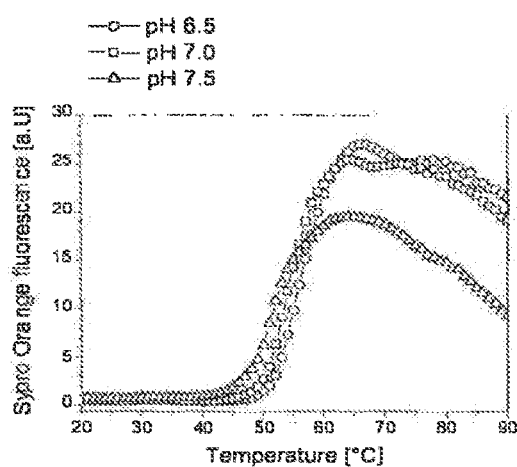
FIG. 4A to 4D depicts melting temperature Tm of citrate buffered husFcγRIIB formulations measured by Differential Scanning Fluorimetry. Use of 0.5 mg/mL husFcγRIIB in 10 mM citrate, 4.5% sugar (2:1 (w/w) sucrose:mannitol), 75 mM NaCl at the indicated pH (FIG. 4A and FIG. 4C), or 0.5 mg/mL husFcγRIIB in 10 mM citrate pH 7.0 supplemented with the indicated amount of sugar (2:1 (w/w) sucrose: mannitol) and salt (FIG. 4B and FIG. 4D). husFcγRIIB formulations were heated in a 96 well microtiter plate at 1° C./min in the presence of Sypro Orange and the fluorescence emission at 610 nm was recorded. The fluorescence vs. temperature plots (FIG. 4A and FIG. 4B) and their first derivatives (FIG. 4C and FIG. 4D) are shown. The first maximum in the dF/dT plots was defined as husFcγRIIB melting temperature.
Figure 4B:
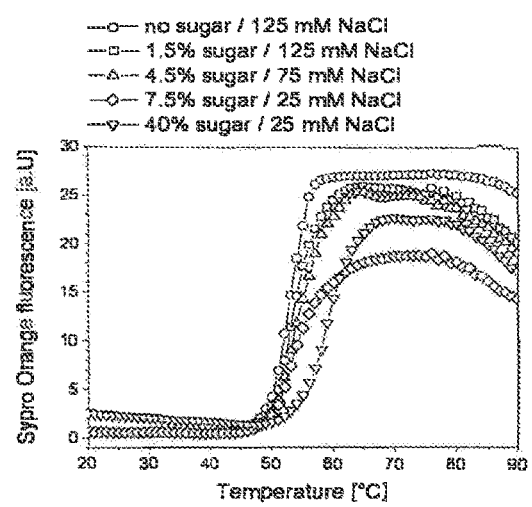
Figure 4C:
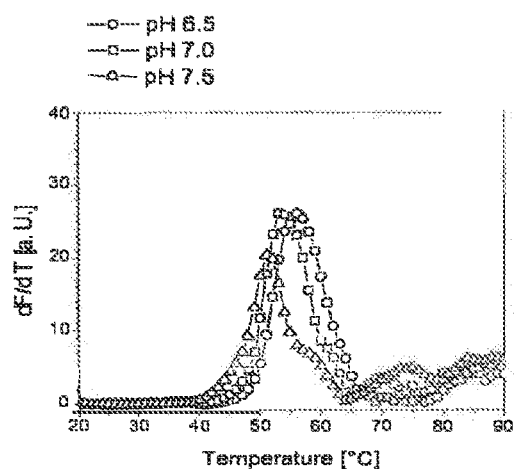
Figure 4D:
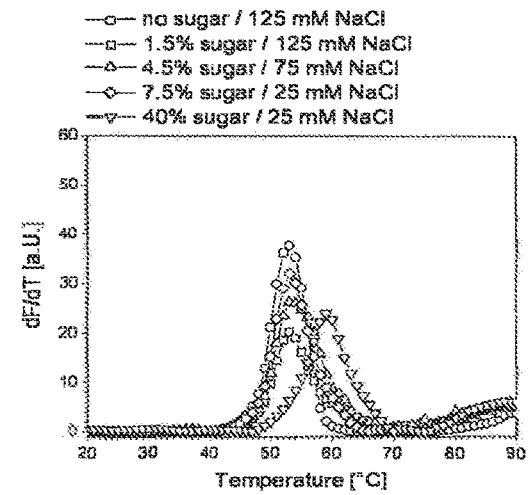

FIG. 3 shows an experiment in which husFcγRIIB crystallisation was performed in 10 mM histidine, 10 mM NaCl as a function of pH. husFcγRIIB in 10 mM hisitidine, 10 mM NaCl pH 5.5 was concentrated to 140 mg/mL by ultrafiltration and diluted to 40 mg/mL with appropriate stock solutions. The crystal yield was determined by measuring the husFcγRIIB concentration in the supernatant after 3 d at 2.8'° C. Each solution contained 0.01% polysorbate 20.

Within a pH range of at least 0.5 units, more than 93% of histidine buffered husFcγRIIB can be crystallized. With a total husFcγRIIB concentration of 40 mg/mL the solubility limit of husFcγRIIB in 10 mM histidine, 10 mM NaCl pH 6.7-7.2 is below 2.8 mg/mL. At pH 6.9 the crystallization was complete in less than one hour at 25° C.

c) husFcγRIIB Solubility Screens

In order to define so called solubility sweet spots, i.e. conditions where husFcγRIIB remains soluble above 100 mg/mL and does not crystallize, various husFcγRIIB formulations were prepared in a 384 well microtiter plate and incubated for at least 4 weeks at 2-8° C. Parameters included into the screen were husFcγRIIB concentration (70, 100, 120, and 150 mg/mL), buffering species (histidine or citrate), pH (5.5, 6.0, 6.5, 7.0, 7.5), NaCl concentration (10-225 mM) and sugar content (0-7.5%). The initial screens at 70 mg/mL (Table 2 and Table 5) and 100 mg/mL husFcγRIIB (Table 3 and Table 6) were conducted with two sugar levels (0% or 3%) and four different NaCl concentrations (10, 50, 225 mM).

Basically these prescreens reproduced the results that were already obtained during the above mentioned concentration screen (Example 2a) and crystallization screens (Example 2b). Histidine buffered husFcγRIIB crystallizes above pH 5.5, whereas citrate buffered husFcγRIIB crystallizes at pH 5.5 to 6.0. Increasing NaCl or sugar concentrations reduced the crystallization process in both cases.

In all subsequent screens at 120 mg/mL and 150 mg/mL husFcγRIIB, only formulations that are isotonic with blood, i.e. with a calculated osmolality around 308 mOsmol/kg were included. For that reason high sugar concentrations were matched with low concentrations of NaCl and vice versa. Histidine based formulations with 120 mg/mL husFcγRIIB were able to prevent crystallization of husFcγRIIB under neutral pH and high ionic strength but with one exception all histidine based formulations at 150 mg/mL husFcγRIIB showed strong crystal growth after 4 weeks at 2-8° C. (Table 4). On the other hand, citrate based formulations were stable up to 150 mg/mL husFcγRIIB from pH 6.5 to 7.5 and at all sugar/salt combinations tested (Table 7).

Therefore citrate buffered husFcγRIIB represents the best basis for the development of a high concentrated liquid formulation suitable for subcutaneous application, i.e. with physiologic pH and tonicity.

d) Thermal Stability of High Concentrated husFcγRIIB Formulations

The formation of non-native protein aggregates and particulates could pose a major obstacle for the development of a high concentrated protein formulation (Shire et al., 2010, Chapter 15. High-concentration antibody formulations. In Formulation and Process Development Strategies for Manufacturing Biopharmaceuticals. Jameel, F. & Hershenson, S., eds., John Wiley, Hoboken, NJ). For that reason formulation candidates (c.f. Example 2c) were ranked in respect to their ability to preserve husFcγRIIB's native structure in the presence of thermal stress and hence prohibit non-native aggregation.

At first the melting temperature $T_m$ of citrate buffered husFcγRIIB formulations was measured by Differential Scanning Fluorimetry. FIG. 4 shows the respective results that were obtained using 0.5 mg/mL husFcγRIIB in 10 mM citrate, 4.5% sugar (2:1 (w/w) sucrose:mannitol), 75 mM NaCl at the indicated pH (FIGS. 4 (a) and (c)), or 0.5 mg/mL husFcγRIIB in 10 mM citrate pH 7.0 supplemented with the indicated amount of sugar (2:1 (w/w) sucrose:mannitol) and salt (FIGS. 4 (b) and (d)). husFcγRIIB formulations were heated in a 96 well microtiter plate at 1° C./min in the presence of Sypro Orange and the fluorescence emission at 610 nm was recorded. The fluorescence vs. temperature plots (a) and (b) and their first derivatives (c) and (d) are shown. The first maximum in the dF/dT plots was defined as husFcγRIIB melting temperature.

Figure 5:
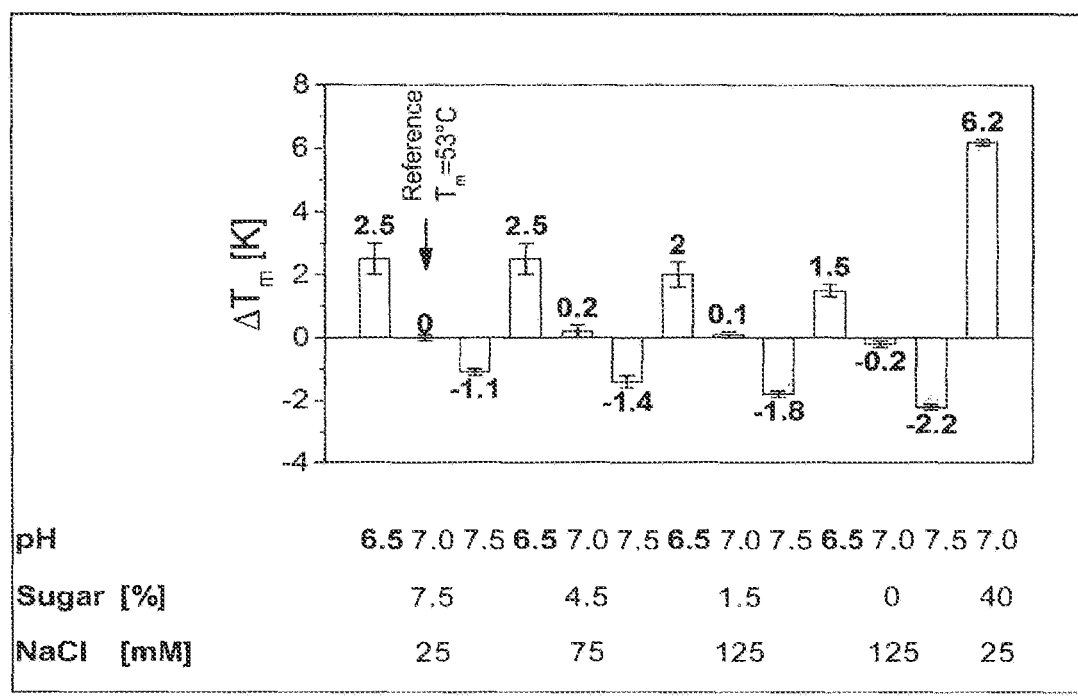
FIG. 5 depicts the change of husFcγRIIB melting temperature as a function of pH, sugar and salt concentration in 10 mM citrate. The average and standard deviation from three independent wells are shown.

Depending on the composition of the respective formulation candidate $T_m$ values from 50.8° C. to 55.5° C. were measured. The largest influence on the melting temperature had the pH with a $T_m$ increase by approx. 3.5° C. when the pH was lowered from 7.5 to 6.5. Addition of 7.5% sugar increased the $T_m$ by approx. 1° C. (FIG. 5, showing the change of the husFcγRIIB melting temperature as a function of pH, sugar and salt concentration in 10 mM citrate. The average and standard deviation from three independent wells are shown). Although the NaCl concentration was lowered in parallel the increased thermal stability is clearly a function of the increased sugar concentration and not the decreased salt content, as shown in earlier experiments (data not shown) and according to the theory of preferential exclusion (Timasheff, 1992, Chapter 9. Stabilization of Protein Structure. In Stability of Protein Pharmaceuticals, Part B: In vivo pathways of degradation and strategies for protein stabilization. Ahern, T. J. & Manning, M. C., eds., Plenum Press, New York, pp. 265-285). This is also exemplified by raising the sugar concentration from 7.5% to 40% which resulted in a $T_m$ increase by 6.2° C.

Next it was determined to what extent the stabilization of husFcγRIIB's secondary and tertiary structure, as indicated by a high melting temperature, would inhibit the formation of insoluble protein aggregates. Therefore the turbidity of citrate buffered husFcγRIIB formulations was measured after incubation at 37° C., a temperature well below the measured $T_m$. To this purpose, the accelerated stability of citrate buffered husFcγRIIB formulations at 37° C. were determined. The optical density at 360 nm was measured as a function of husFcγRIIB concentration and sucrose concentration after 1 h (a), 12 h (b) and 7 d (c). All formulations contained 10 mM citrate pH 7.0, 25 mM NaCl. The optical density of a buffer control was subtracted. At 40% sucrose, the highest concentrated formulation contained only 60 mg/mL husFcγRIIB and not 80 mg/mL.

Figure 6A:
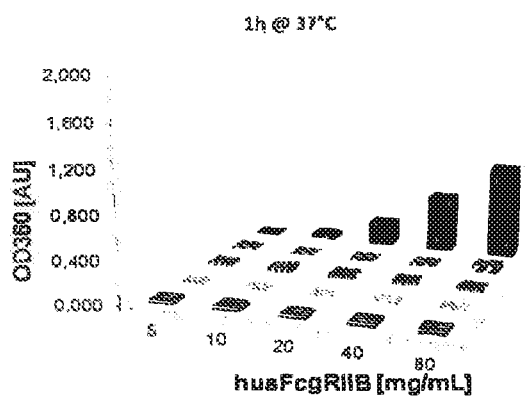
FIG. 6A to 6C depicts turbidity of citrate buffered husFcγRIIB formulations. Optical density at 360 nm was measured as a function of husFcγRIIB concentration and sucrose concentration after 1 h (FIG. 6A), 12 h (FIG. 6B) and 7 d (FIG. 6C). All formulations contained 10 mM citrate pH 7.0, 25 mM NaCl. The optical density of a buffer control was subtracted. At 40% sucrose, the highest concentrated formulation contained only 60 mg/mL husFcγRIIB and not 80 mg/mL.
Figure 6B:
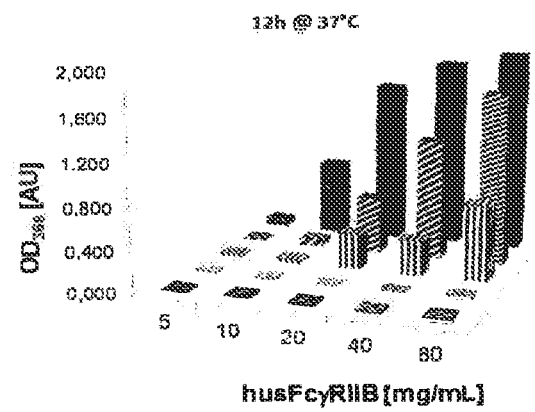
Figure 6C:
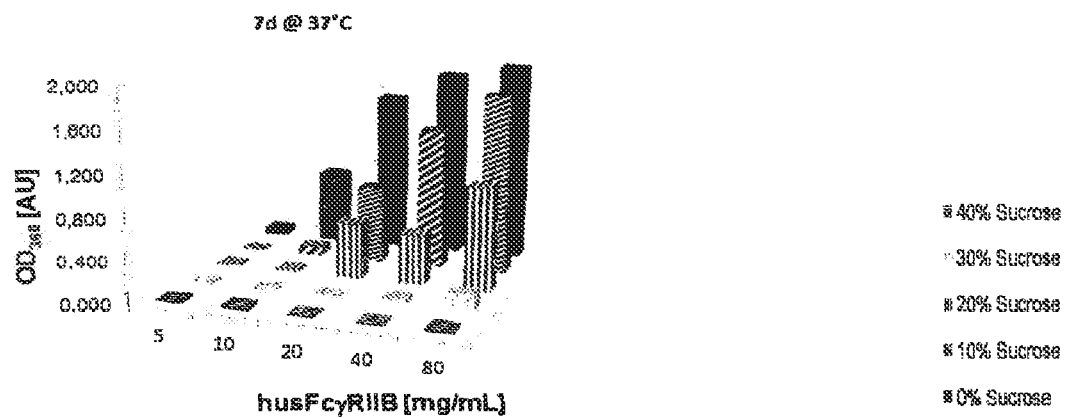

The results are shown in FIG. 6. With increasing sucrose concentration (increasing concentrations from back to front on z-axis in all diagrams of FIG. 6), i.e. increasing melting temperature of the protein, the rise in turbidity is retarded. With no added sucrose all formulations with a strength 10 mg/mL husFcγRIIB became already turbid after one hour at 37° C., whereas at 40% sucrose no significant increase in turbidity up to 60 mg/mL husFcγRIIB was observed even after seven days at 37° C. Above a certain protein concentration the absolute turbidity increases linearly with increasing husFcγRIIB concentration but below that threshold the formation of insoluble protein aggregates is extremely slow or even inhibited. With increasing sucrose concentrations this threshold is shifted to higher husFcγRIIB concentrations, but from the physiologic point of view unacceptable high sucrose concentrations will be needed to stabilize husFcγRIIB at 37° C. and a concentration exceeding 60 mg/mL.

Figure 7A:
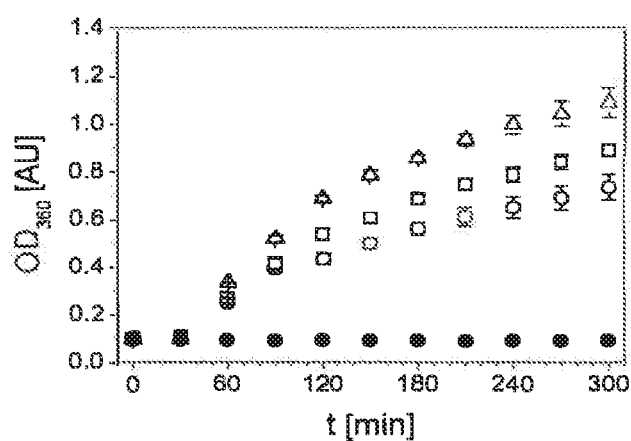
FIG. 7A to 7B depicts accelerated stability of citrate buffered husFcγRIIB formulations at 40° C. The increase in optical density at 360 nm was measured at 10 mg/mL husFcγRIIB in 10 mM citrate, 150 mM NaCl pH 7.0 supplemented with 10%/292 mM sucrose (FIG. 7A, Δ), 10%/292 mM trehalose (FIG. 7A, €), 5%/274 mM mannitol (FIG. 7A, ○), 30%/876 mM sucrose (FIG. 7B, Δ), 30%/876 mM trehalose (FIG. 7B, €), 15%/822 mM mannitol (FIG. 7B, ○). The buffer control supplemented with 20% sucrose is also shown (•).
Figure 7B:
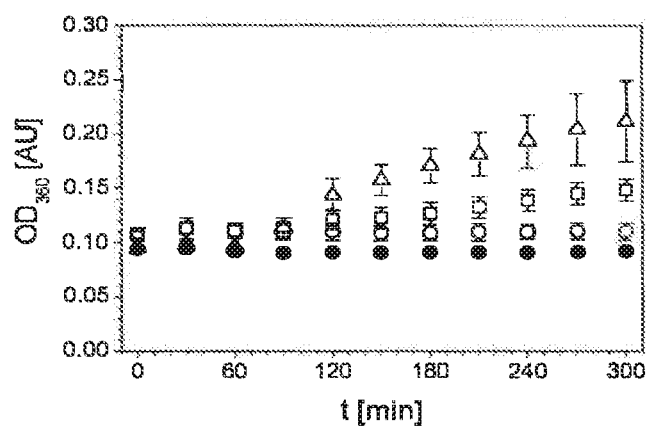

A further test was conducted regarding the accelerated stability of citrate buffered husFcγRIIB formulations at 40° C. The results are shown in FIG. 7. The increase in optical density at 360 nm was measured at 10 mg/mL husFcγRIIB in 10 mM citrate, 150 mM NaCl pH 7.0 supplemented with 10%/292 mM sucrose (a, △), 10%/292 mM trehalose (a, □), 5%/274 mM mannitol (a, ○), 30%/876 mM sucrose (b, △), 30%/876 mM trehalose (b, □), 15%/822 mM mannitol (b, ○). The buffer control supplemented with 20% sucrose is also shown (•).

Based on these observations different sugars and sugar alcohols were ranked in respect to their ability to suppress the formation of insoluble protein aggregates. As shown in FIG. 7, the most efficient stabilizer is sucrose.

e) Definition of Required Detergent Concentration

Turbidity assays (data not shown) indicated in accordance with published data (Timasheff, 1992, Chapter 9. Stabilization of Protein Structure. In Stability of Protein Pharmaceuticals, Part B: In vivo pathways of degradation and strategies for protein stabilization. Ahern, T. J. & Manning, M. C., eds., Plenum Press, New York, pp. 265-285) that increasing detergent concentrations destabilize husFcγRIIB. Also it is speculated that the use of high detergent concentrations may lead to increased immunogenicity (Hermeling et al., 2003, Pharm. Res. 20, 1903-1907). For that reason it would be mandatory to keep the detergent concentration as low as possible without compromising its stabilizing effect towards surface stress.

Ideally, the polysorbate 20 concentration would be fixed at 0.005%, the concentration which is used for already established liquid husFcγRIIB formulations containing 5-20 mg/mL husFcγRIIB. But since the strength of the newly developed formulation will be above 50 mg/mL and polysorbate 20 may bind to the protein, it was questioned whether the detergent concentration must be raised above 0.005%.

In order to test the hypothesis of unspecific detergent binding by the protein a citrate buffered formulation candidate containing 0.005% polysorbate 20 was supplied with increasing concentrations of husFcγRIIB and the solutions were incubated for one hour at room temperature and 60° C., a temperature well above the determined $T_m$ of husFcγRIIB. After the protein and hypothetically bound polysorbate 20 were removed by cation exchange chromatography the amount of free polysorbate was measured. In FIG. 8 an experiment is shown that determines free polysorbate 20 in the presence of husFcγRIIB. husFcγRIIB in 10 mM citrate, 25 mM NaCl, 3% sucrose, 1.5% mannitol, 0.005% polysorbate 20, pH 6.7 was incubated for 1 h at 25° C. (native husFcγRIIB) and 60° C. (denatured husFcγRIIB). After husFcγRIIB was removed by cation exchange chromatography (CEX), the amount of polysorbate 20 was measured (a). The blank represents buffer without added husFcγRIIB or detergent. The system suitability tests (SST) represent buffer with 0.005% polysorbate 20, SST2 was CEX treated and SST1 not. The measured polysorbate content at 0.08-0.72 mg/mL husFcγRIIB was extrapolated to husFcγRIIB concentrations above 10 mg/mL by linear regression ($R^2>0.998$) of the polysorbate concentration versus the logarithmic husFcγRIIB concentration (b).

As shown in FIG. 8, a linear relationship between the free polysorbate content and the logarithmic husFcγRIIB concentration was established. Therefore it is expected that the concentration of free polysorbate will only change marginally, by approx. 0.0001-0.0002%, in case that the strength of the formulation is increased from 20 to 100 mg/mL. The significantly lower polysorbate concentration in the samples compared to the control at 0.005% is largely attributed to the fact the samples were diluted with CEX equilibration buffer, which was prepared without polysorbate 20, during column loading (c.f. FIG. 8 SST 1 vs. SST2).

f) Viscosity of High Concentrated husFcγRIIB Formulations

Highly concentrated protein formulations are characterized by a high viscosity (Shire et al., 2010, supra). Therefore the manufacturability of a highly concentrated protein formulation might be hampered by its viscosity as the concentration process by tangential flow filtration may become unacceptable slow. In a further experiment, the solution viscosity of husFcγRIIB in 10 mM citrate, 25 mM NaCl, pH 7.0 was measured at 20° C.

Figure 9:
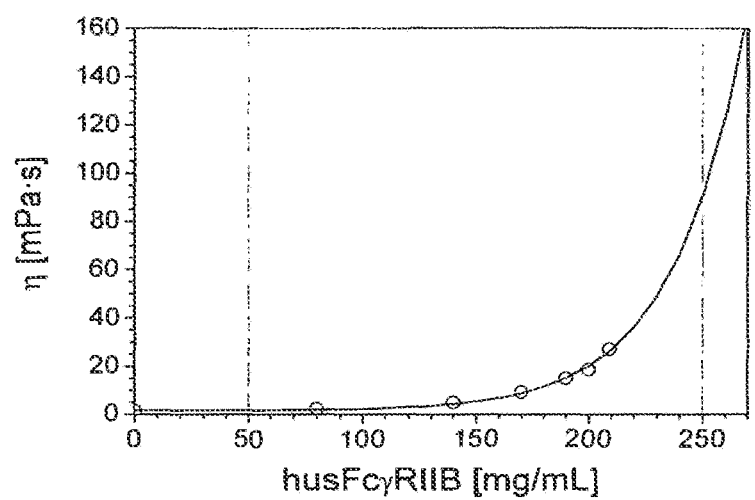
FIG. 9 depicts solution viscosity of husFcγRIIB in 10 mM citrate, 25 mM NaCl, pH 7.0 was measured at 20° C. (○) was fitted to an exponential growth function (-, $R^2>0.992$) and found that the solution viscosity of the formulation is low enough to run economic TFF processes up to at least 210 mg/mL.
Figure 10:
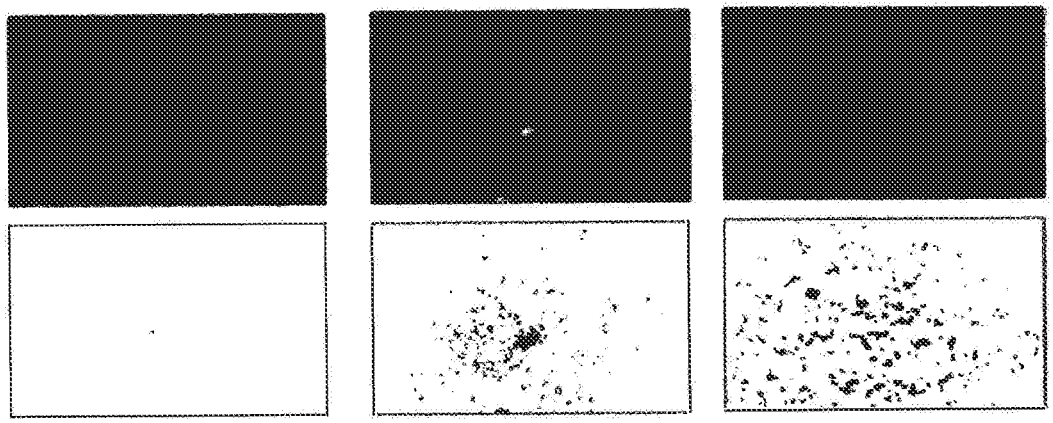
FIG. 10 depicts particulate load of selected formulations as determined by fluorescence microscopy. All formulations contained 5 mM citrate pH 6.7 and the indicated amount of salt, sugar and detergent. The formulations were lyophilized and reconstituted to the indicated husFcγRIIB content.

The experimental data as shown in FIG. 9 (○) was fitted to an exponential growth function (-, $R^2>0.992$) and found that the solution viscosity of the formulation is low enough to run economic TFF processes up to at least 210 mg/mL.

g) Lyophilisation of husFcγRIIB Containing Formulations 59 formulations with varying husFcγRIIB, sugar, salt and detergent content were subjected to a conservative lyophilisation cycle. The solids were reconstituted with a volume of water for injection that was equal to or less than the original volume prior to the lyophilisation process. In doing so the husFcγRIIB content after reconstitution was adjusted to a nominal content of 60-180 mg/mL. The suitability of the various formulations for lyophilisation was evaluated based on the reconstitution time and the particulate contamination after reconstitution. Several formulations were identified that could be reconstituted in less than 2 min and neither showed an increased turbidity nor the formation of particulate in the visible and sub-visible range. Based on the above described lyophilisation screen it was shown that ideal formulations contained low amounts of husFcγRIIB (e.g. 15-60 mg/mL) prior to lyophilisation and were reconstituted with low volumes of water for injection, thereby increasing the final detergent concentration. The particulate load of selected formulations as determined by fluorescence microscopy is shown in FIG. 10. All formulations contained 5 mM citrate pH 6.7 and the indicated amount of salt, sugar and detergent. The formulations were lyophilized and reconstituted to the indicated husFcγRIIB content.

What is claimed is:

1. A suspension formulation comprising Fcγ receptor (FcγR) in a crystalline or microcrystalline form, soluble FcγR at a concentration greater than 60 mg/mL, 5 mM to 200 mM NaCl, 2.0% to 8% sugar, and a buffer solution comprising:
   (a) citrate at a concentration of 1 to 50 mM, wherein the pH of the formulation is from 5.2 to 5.9, or
   (b) histidine at a concentration of 1 to 50 mM, wherein the pH of the formulation is from 6.0 to 7.5.

2. The formulation of claim 1, wherein the receptor comprises an FcγRII receptor.

3. The formulation of claim 2, wherein the receptor comprises FcγRIIB.

4. The formulation of claim 1, wherein said formulation further comprises a detergent.

5. The formulation of claim 1, wherein the buffer solution comprises citrate at a concentration of 1 to 50 mM.

6. The formulation of claim 1, wherein the buffer solution comprises histidine at a concentration of 1 to 50 mM.

7. The formulation of claim 1, wherein the Fcγ receptor is present in a crystalline form.

8. The formulation of claim 1, wherein the Fcγ receptor is present in a microcrystalline form.

* * * * *

SEQUENCE LISTING

```
<160> NUMBER OF SEQ ID NOS: 1

<210> SEQ ID NO 1
<211> LENGTH: 177
<212> TYPE: PRT
<213> ORGANISM: Homo sapiens
<220> FEATURE:
<221> NAME/KEY: SEQ ID NO:1
<222> LOCATION: (1)..(177)
<223> OTHER INFORMATION: husFcgammaRIIB

<400> SEQUENCE: 1

Met Ala Pro Pro Lys Ala Val Leu Lys Leu Glu Pro Gln Trp Ile Asn
1               5                   10                  15
```

```
Val Leu Gln Glu Asp Ser Val Thr Leu Thr Cys Arg Gly Thr His Ser
            20                  25                  30

Pro Glu Ser Asp Ser Ile Gln Trp Phe His Asn Gly Asn Leu Ile Pro
        35                  40                  45

Thr His Thr Gln Pro Ser Tyr Arg Phe Lys Ala Asn Asn Asn Asp Ser
    50                  55                  60

Gly Glu Tyr Thr Cys Gln Thr Gly Gln Thr Ser Leu Ser Asp Pro Val
65                  70                  75                  80

His Leu Thr Val Leu Ser Glu Trp Leu Val Leu Gln Thr Pro His Leu
            85                  90                  95

Glu Phe Gln Glu Gly Glu Thr Ile Val Leu Arg Cys His Ser Trp Lys
            100                 105                 110

Asp Lys Pro Leu Val Lys Val Thr Phe Phe Gln Asn Gly Lys Ser Lys
        115                 120                 125

Lys Phe Ser Arg Ser Asp Pro Asn Phe Ser Ile Pro Gln Ala Asn His
    130                 135                 140

Ser His Ser Gly Asp Tyr His Cys Thr Gly Asn Ile Gly Tyr Thr Leu
145                 150                 155                 160

Tyr Ser Ser Lys Pro Val Thr Ile Thr Val Gln Ala Pro Ser Ser Ser
            165                 170                 175

Pro
```